(12) United States Patent
Schuele et al.

(10) Patent No.: US 11,793,675 B2
(45) Date of Patent: Oct. 24, 2023

(54) METHODS AND SYSTEMS FOR CHANGING A REFRACTIVE PROPERTY OF AN IMPLANTABLE INTRAOCULAR LENS

(71) Applicant: AMO Development, LLC, Irvine, CA (US)

(72) Inventors: Georg Schuele, Portola Valley, CA (US); Alexander Vankov, Mountain View, CA (US); Jenny Wang, Mountain View, CA (US); David A. Dewey, Sunnyvale, CA (US); Tianheng Wang, Fremont, CA (US); Michael Wiltberger, Santa Clara, CA (US); Mihai State, Groningen (NL); Phillip Gooding, Mountain View, CA (US)

(73) Assignee: AMO Development, LLC, Irvine, CA (US)

( * ) Notice: Subject to any disclaimer, the term of this patent is extended or adjusted under 35 U.S.C. 154(b) by 0 days.

(21) Appl. No.: 17/451,812

(22) Filed: Oct. 21, 2021

(65) Prior Publication Data
US 2022/0031504 A1 Feb. 3, 2022

Related U.S. Application Data

(63) Continuation of application No. 16/375,784, filed on Apr. 4, 2019, now Pat. No. 11,154,424.
(Continued)

(51) Int. Cl.
*A61F 9/008* (2006.01)
*A61F 2/16* (2006.01)
(Continued)

(52) U.S. Cl.
CPC ............... *A61F 9/008* (2013.01); *A61F 2/16* (2013.01); *A61F 2/1602* (2013.01); *A61F 2/164* (2015.04);
(Continued)

(58) Field of Classification Search
CPC ...... A61F 2/164; A61F 2/1602; A61F 2/1627; A61F 2/1635; A61F 2/1648;
(Continued)

(56) References Cited

U.S. PATENT DOCUMENTS 4,834,750 A 5/1989 Gupta
5,728,156 A 3/1998 Gupta et al.
(Continued)

FOREIGN PATENT DOCUMENTS

EP 2268230 B1 3/2016
WO 2007006470 A1 1/2007
(Continued)

*Primary Examiner* — Paul B Prebilic
(74) *Attorney, Agent, or Firm* — Johnson & Johnson Surgical Vision, Inc.

(57) ABSTRACT

A method of altering a refractive property of a crosslinked acrylic polymer material by irradiating the material with a high energy pulsed laser beam to change its refractive index. The method is used to alter the refractive property, and hence the optical power, of an implantable intraocular lens after implantation in the patient's eye. In some examples, the wavelength of the laser beam is in the far red and near IR range and the light is absorbed by the crosslinked acrylic polymer via two-photon absorption at high laser pulse energy. The method also includes designing laser beam scan patterns that compensate for effects of multiphone absorption such as a shift in the depth of the laser pulse absorption location, and compensate for effects caused by high laser pulse energy such as thermal lensing. The method can be used to form a Fresnel lens in the optical zone.

6 Claims, 25 Drawing Sheets

Related U.S. Application Data

(60) Provisional application No. 62/720,882, filed on Aug. 21, 2018, provisional application No. 62/654,192, filed on Apr. 6, 2018.

(51) Int. Cl.
| | | |
|---|---|---|
| *B29D 11/02* | (2006.01) | |
| *B29C 71/04* | (2006.01) | |
| *G02C 7/02* | (2006.01) | |
| *B29D 11/00* | (2006.01) | |
| *B29C 35/08* | (2006.01) | |

(52) U.S. Cl.
CPC ............ *A61F 2/1627* (2013.01); *B29C 71/04* (2013.01); *B29D 11/00461* (2013.01); *B29D 11/023* (2013.01); *G02C 7/022* (2013.01); *A61F 2/1635* (2013.01); *A61F 2/1648* (2013.01); *A61F 2002/1681* (2013.01); *A61F 2009/0087* (2013.01); *A61F 2009/00842* (2013.01); *A61F 2009/00851* (2013.01); *A61F 2250/0053* (2013.01); *A61L 2430/16* (2013.01); *B29C 2035/0838* (2013.01); *B29C 2791/009* (2013.01); *B29K 2995/0031* (2013.01); *G02C 2202/12* (2013.01)

(58) Field of Classification Search
CPC .... A61F 2009/00851; A61F 2250/0004; A61F 2250/0053; B29D 11/023; A61L 2430/16
See application file for complete search history.

(56) References Cited

U.S. PATENT DOCUMENTS

| | | |
|---|---|---|
| 6,548,693 B2 | 4/2003 | Piccolo et al. |
| 6,609,673 B1 | 8/2003 | Johnson |
| 7,237,893 B2 | 7/2007 | Chang et al. |
| 7,278,737 B2 | 10/2007 | Mainster et al. |
| 7,615,073 B2 | 11/2009 | Deacon et al. |
| 7,896,916 B2 | 3/2011 | Piers et al. |
| 8,109,999 B2 | 2/2012 | Hampp |
| 8,512,320 B1 | 8/2013 | Knox et al. |
| 8,845,625 B2 | 9/2014 | Angeley et al. |
| 8,932,352 B2 | 1/2015 | Knox et al. |
| 9,060,847 B2 | 6/2015 | Smith et al. |
| 9,144,491 B2 | 9/2015 | Knox et al. |
| 2005/0027031 A1* | 2/2005 | Chang ...................... C08F 2/50 522/68 |
| 2011/0172649 A1 | 7/2011 | Schuele et al. |
| 2013/0103144 A1 | 4/2013 | Bille et al. |
| 2014/0135920 A1 | 5/2014 | Sahler et al. |
| 2015/0258240 A1 | 9/2015 | Grubbs |
| 2015/0335477 A1 | 11/2015 | Schuele et al. |
| 2016/0144580 A1 | 5/2016 | Knox et al. |
| 2016/0229132 A1 | 8/2016 | Risser |
| 2016/0296662 A1 | 10/2016 | Stoy et al. |
| 2016/0339657 A1 | 11/2016 | Grubbs et al. |
| 2017/0015693 A1 | 1/2017 | Carlson et al. |
| 2019/0001024 A1* | 1/2019 | Grubbs ................. A61L 27/047 |
| 2021/0128294 A1 | 5/2021 | Knox et al. |
| 2021/0177579 A1 | 6/2021 | Zheleznyak et al. |

FOREIGN PATENT DOCUMENTS

| | | |
|---|---|---|
| WO | 2011123484 A2 | 10/2011 |
| WO | 2017106321 A1 | 6/2017 |
| WO | 2018152407 A1 | 8/2018 |

* cited by examiner

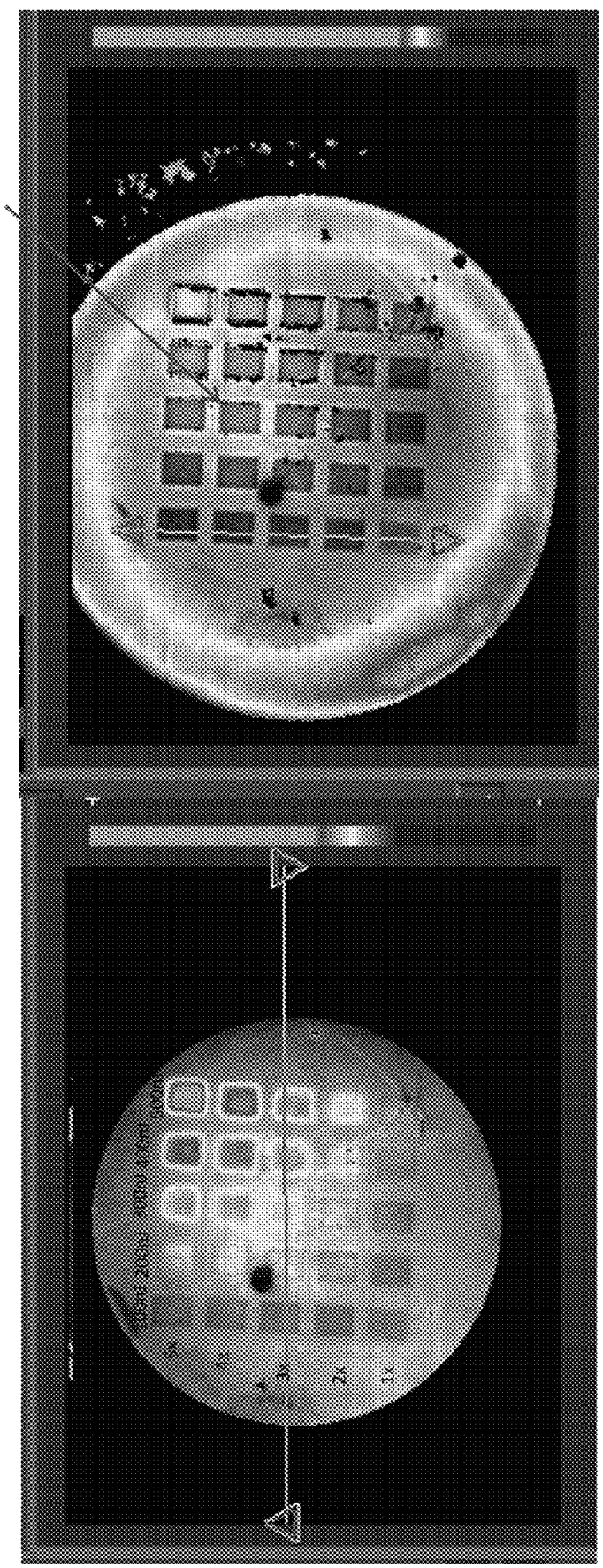

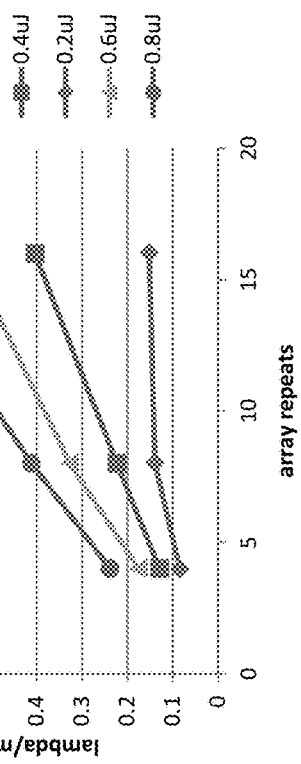
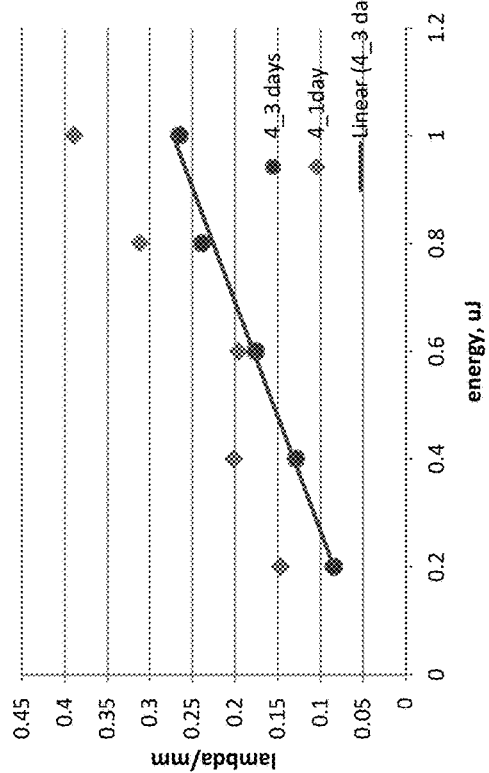
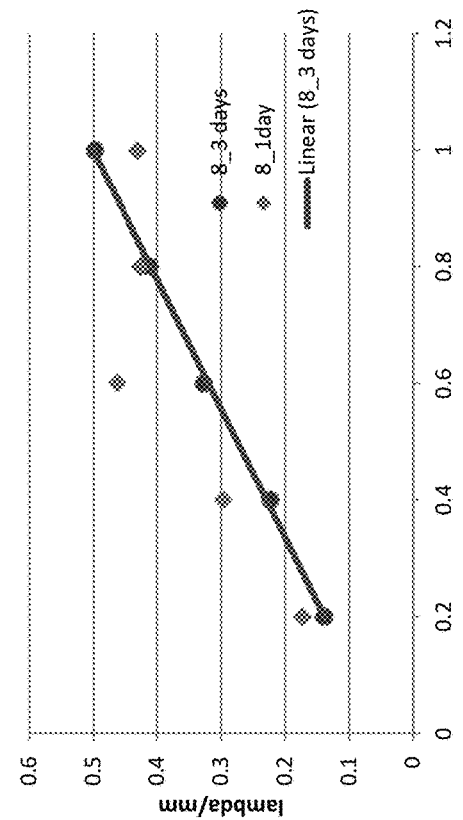
FIG. 8A
FIG. 8B
FIG. 8C

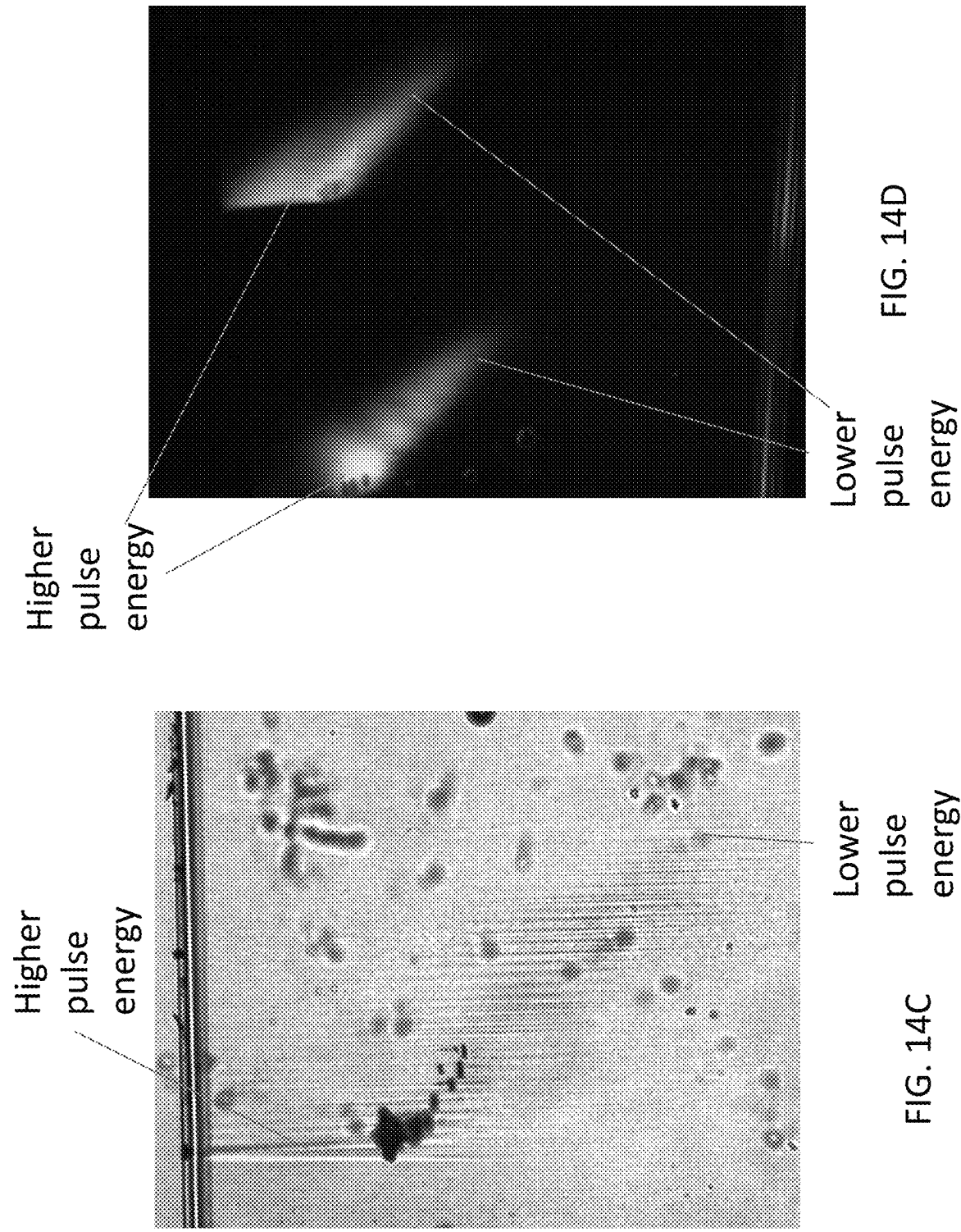

METHODS AND SYSTEMS FOR CHANGING A REFRACTIVE PROPERTY OF AN IMPLANTABLE INTRAOCULAR LENS

CROSS REFERENCE TO RELATED APPLICATIONS

This application claims priority to and is a continuation of U.S. patent application Ser. No. 16/375,784, filed Apr. 4, 2019, now U.S. Pat. No. 11,154,424, which claims the benefit under 35 U.S.C. § 119(e) of U.S. Provisional Patent Application Nos. 62/654,192, filed Apr. 6, 2018 and 62/720,882, filed Aug. 21, 2018. The contents of the above applications are incorporated herein by reference in their entireties.

BACKGROUND OF THE INVENTION

Cataract extraction is one of the most commonly performed surgical procedures in the world. A cataract is the opacification of the crystalline lens or its envelope—the lens capsule—of the eye. It varies in degree from slight to complete opacity that obstructs the passage of light. Early in the development of age-related cataract the power of the lens may be increased, causing near-sightedness (myopia), and the gradual yellowing and opacification of the lens may reduce the perception of blue colors as those wavelengths are absorbed and scattered within the crystalline lens. Cataract typically progresses slowly to cause vision loss and are potentially blinding if untreated.

Treatment is performed by removing the opaque crystalline lens and replacing it with an artificial intraocular lens (IOL). An estimated 3 million cases are presently performed annually in the United States and 15 million worldwide. This market is composed of various segments including intraocular lenses for implantation, viscoelastic polymers to facilitate surgical maneuvers, disposable instrumentation including ultrasonic phacoemulsification tips, tubing, and various knives and forceps.

However, post-surgical visual acuity in patients with a newly implanted IOL is often imperfect. There is a need for improved methods of correcting the refractive properties of an IOL after implantation in order to improve post-surgical outcomes.

SUMMARY OF THE INVENTION

In many embodiments, a method of altering a refractive property of a crosslinked acrylic polymer comprises generating a light beam with a light source; and irradiating the crosslinked acrylic polymer with the light beam, thereby producing a predetermined change in a refractive property of the crosslinked acrylic polymer. Preferably, irradiation with the laser light beam results in a change in refractive index of the cross-linked acrylic polymer, thereby causing the predetermined change in the refractive property. In many embodiments, a first change in the refractive index is negative during a first time period after irradiation and a second change in the refractive index is positive in a second time period after irradiation. In many embodiments, a change in refractive index of the cross-linked acrylic polymer relative to the pre-irradiation refractive index at a location within the crosslinked acrylic polymer is linearly related with a total energy of the irradiation with the light source.

In preferred embodiments, the light source is a pulsed laser source, and the pulsed laser source produces femtosecond or longer up to a few nanosecond laser pulse. In preferred embodiments, the pulsed laser pulses irradiate the crosslinked acrylic polymer and produce a first change in the refractive index which is negative during a first time period after irradiation and a second change in the refractive index which is positive in a second time period after irradiation. The first time period may occur either before or second time period, i.e. the change may be negative and then becomes positive, or vice versa. This predetermined change in refractive index relative to the pre-irradiation refractive index at a location within the crosslinked acrylic polymer is determined by controlling a total energy of the irradiation with the light source.

A method of altering a refractive property of an implantable intraocular lens having an optic body including an optical zone and a peripheral zone entirely surrounding the optical zone, comprises generating a light beam with a light source; and irradiating the optical zone with the light beam. The optical zone comprises a crosslinked acrylic material and irradiation with the light beam produces a predetermined change in a refractive property of the crosslinked acrylic polymer, thereby altering a refractive property of the intraocular lens. Preferably, irradiation with the laser light beam results in a change in refractive index of the crosslinked acrylic polymer, thereby causing the predetermined change in the refractive property. Preferably, first change in the refractive index is negative during a first time period after irradiation and a second change in the refractive index is positive in a second time period after irradiation, and becomes stable over a long period of time. Preferably, the change in refractive index relative to the pre-irradiation refractive index at a location within the crosslinked acrylic polymer is linearly related with a total energy of the irradiation with the light source.

In another aspect, the present invention provides a method of altering a refractive property of an implantable intraocular lens having an optic body including an optical zone and a peripheral zone surrounding the optical zone, the method including: generating a light beam using a light source and a light delivery optical system; and irradiating the optical zone with the light beam, wherein the optical zone comprises a material configured to change its refractive index upon irradiation by the light beam, thereby altering a refractive property of the intraocular lens.

In some embodiments, the optical zone comprises a crosslinked acrylic material, and wherein irradiation with the light beam produces a predetermined change in the refractive index of the crosslinked acrylic polymer. In some embodiments, the intraocular lens is implanted in a patient's eye before the irradiating step, and the light beam with a wavelength of 400 to 450 nm or 650 to 800 nm is used.

In some embodiments, the light source is a pulsed laser source, and irradiating step includes scanning a focus spot of the pulsed laser beam within the optical zone of the intraocular lens according to a scan pattern. In some embodiment, the scan pattern is designed to compensate for a multi-photon absorption-induced shift in absorption depth. In some embodiments, the scan pattern is designed to compensate for a thermal lensing effect, which is an optical effect on subsequent laser pulses caused by a temperature gradient induced by previous laser pulses. In some embodiments, the scan pattern includes forming a plurality of layers (or lines, or spots) in an interlaced manner such that any layers that are immediately adjacent each other in their spatial order are not immediately adjacent each other in the time order in which they are formed. In some embodiments, the scan pattern in the optical zone is configured to produce a refractive index modification profile of a Fresnel lens.

This summary and the following detailed description are merely exemplary, illustrative, and explanatory, and are not intended to limit, but to provide further explanation of the invention as claimed. Additional aspects, features, objectives and advantages of the invention will be set forth in the descriptions that follow, and in part will become apparent from the written description, taken in conjunction with the accompanying drawings, illustrating by way of example the principles of the invention, or may be learned by practice of the invention.

BRIEF DESCRIPTION OF THE DRAWINGS

FIG. 6A shows an image of a change in index of refraction of an acrylic material irradiated with a femtosecond material at 1 hour after exposure as a function of pulse energy and number of repeat pulse exposures. Pulse energy is increased from 0.1 µJ to 0.5 µJ for 1-5 repeats of the laser pulses. A blue color indicates a positive index change. A red color indicates a negative index change. FIG. 6B represents the same sample 1 day after treatment. Note that the outlines of the squares on the upper right stays after diffusion process and the sign of the index modification has changed from 1 hour to 1 day.

FIG. 8A is a graph of index of refraction vs. pulse energy (micro Joules) for a crosslinked acrylic material irradiated with a femtosecond laser with 4 repeat laser pulses at 1 and 3 days post irradiation. Note that the index of refraction change of the acrylic material is linear with total energy at 3 days post irradiation.

FIG. 8B is a graph of laser pulse energy (micro Joules) vs. index of refraction for a crosslinked acrylic material irradiated with a femtosecond laser with 8 repeat laser pulses at 1 and 3 days post irradiation. Note that the index of refraction change of the acrylic material is linear with total energy at 3 days post irradiation.

FIG. 8C is a graph of index of refraction vs. pattern repeats for an acrylic material irradiated with a femtosecond laser at 3 days post irradiation. Note that the index of refraction change of the acrylic material is generally linear with the number of pattern repeats at 3 days post irradiation.

FIG. 10A is an image of the index change in a crosslinked acrylic material irradiated with a 0.6 ns pulse laser, with a repetition rate of 30 kHz, a pulse energy of 6.6 uJ, of spot size 1.5 um, with 1, 2, 4, 8 and 16 irradiation repeats.

FIGS. 14A-14D illustrate the spatial distribution of pulse energy absorption near the focus point due to multi-photon absorption in the volume above the focus point. FIG. 14 A shows a graphical representation of the absorbed energy moving towards the incident laser pulse due to the two photon absorption. FIG. 14B shows similar simulation results of a low and high energy laser pulse applied at the same focal depth but due to the higher two photon absorption most of the energy of the high energy pulse is absorbed above the laser focus. FIG. 14C shows this effect in a sample in which the same focal depth was irradiated in the acrylic material at different energies demonstrating the focus change towards the incident laser. FIG. 14D shows the exposed sample cross section with high lightened fluorescence of the lasered area.

DETAILED DESCRIPTION OF THE INVENTION

Figure 1:
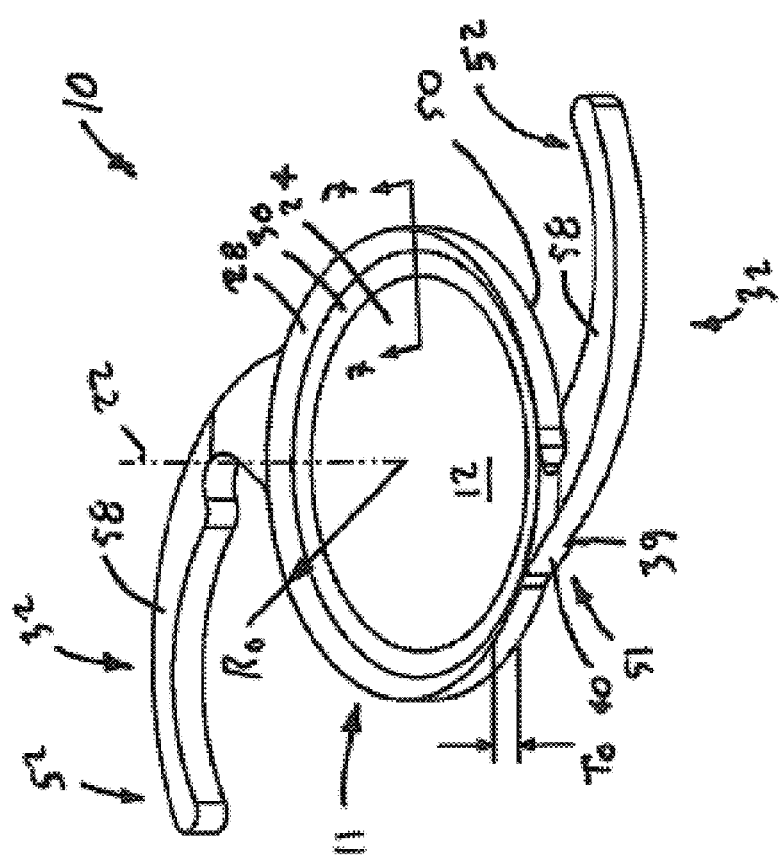
FIG. 1 is a perspective view illustrating the anterior surface of an intraocular lens according to one embodiment of the present invention.

In many embodiments, a method of altering a refractive property of a crosslinked acrylic polymer comprises generating a light beam with a light source; and irradiating the crosslinked acrylic polymer with the light beam, thereby producing a predetermined change in a refractive property of the crosslinked acrylic polymer. Preferably, irradiation with the laser light beam results in a change in refractive index of the cross-linked acrylic polymer, thereby causing the predetermined change in the refractive property. In some embodiments, a first change in the refractive index is negative during a first time period after irradiation and a second change in the refractive index is positive in a second time period after irradiation. In some embodiments, a change in refractive index of the cross-linked acrylic polymer relative to the pre-irradiation refractive index at a location within the crosslinked acrylic polymer is linearly related with a total energy of the irradiation with the light source.

In preferred embodiments, the light source is a pulsed laser source, and the pulsed laser source produces at least one of femtosecond laser pulse and picosecond laser pulses. In the preferred embodiments, the pulsed laser pulses irradiate the crosslinked acrylic polymer and produce a first change in the refractive index is negative during a first time period after irradiation and a second change in the refractive index is positive in a second time period after irradiation. The first time period may occur either before or second time period. The predetermined change in refractive index relative to the pre-irradiation refractive index at a location within the crosslinked acrylic polymer is determined by controlling a total energy of the irradiation with the light source.

A method of altering a refractive property of an implantable intraocular lens having an optic body including an optical zone and a peripheral zone entirely surrounding the optical zone, comprises generating a light beam with a light source; and irradiating the optical zone with the light beam. The optical zone comprises a crosslinked acrylic material and irradiation with the light beam produces a predetermined change in a refractive property of the crosslinked acrylic polymer, thereby altering a refractive property of the intraocular lens. Preferably, irradiation with the laser light beam results in a change in refractive index of the cross-linked acrylic polymer, thereby causing the predetermined change in the refractive property. Preferably, first change in the refractive index is negative during a first time period after irradiation and a second change in the refractive index is positive in a second time period after irradiation. Preferably, the change in refractive index relative to the pre-irradiation refractive index at a location within the cross-linked acrylic polymer is linearly related with a total energy of the irradiation with the light source.

Preferably, the light source is a pulsed laser source. The pulsed laser source produces femtoseconds or longer up to a few nanoseconds laser pulses. A first change in the refractive index caused by irradiation with the pulsed laser is negative during a first time period after irradiation and a second change in the refractive index is positive in a second time period after irradiation. Preferably, the change in refractive index relative to the pre-irradiation refractive index at a location within the crosslinked acrylic polymer is linearly related with a total energy of the irradiation with the light source.

Figure 2:
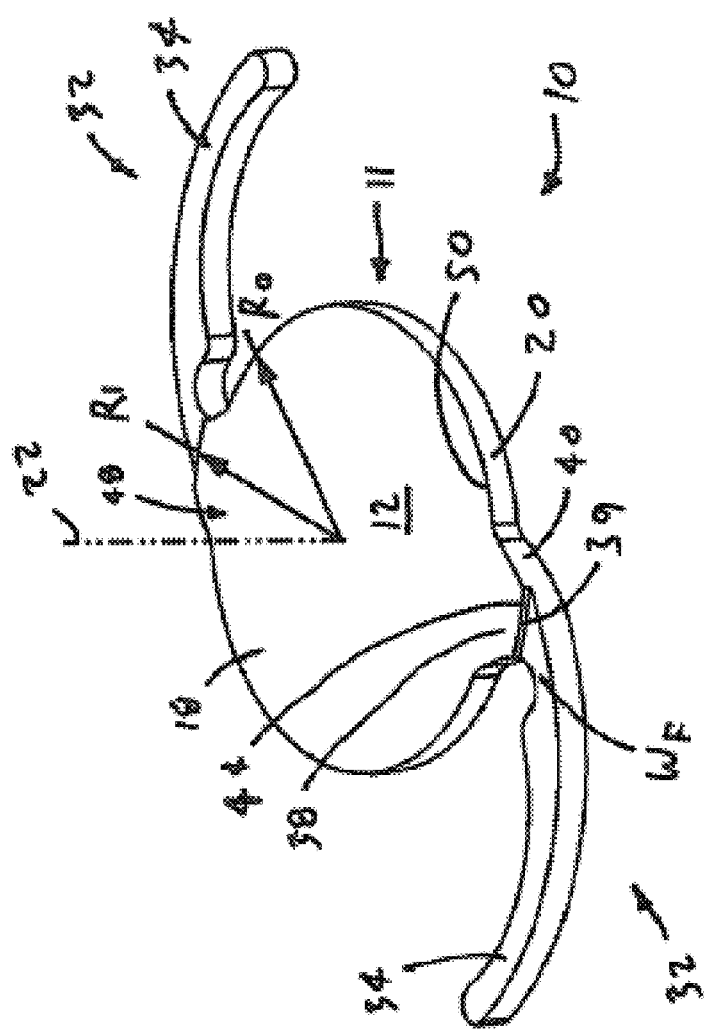
FIG. 2 is a perspective view illustrating the posterior surface of the intraocular lens shown in FIG. 1.
Figure 3:
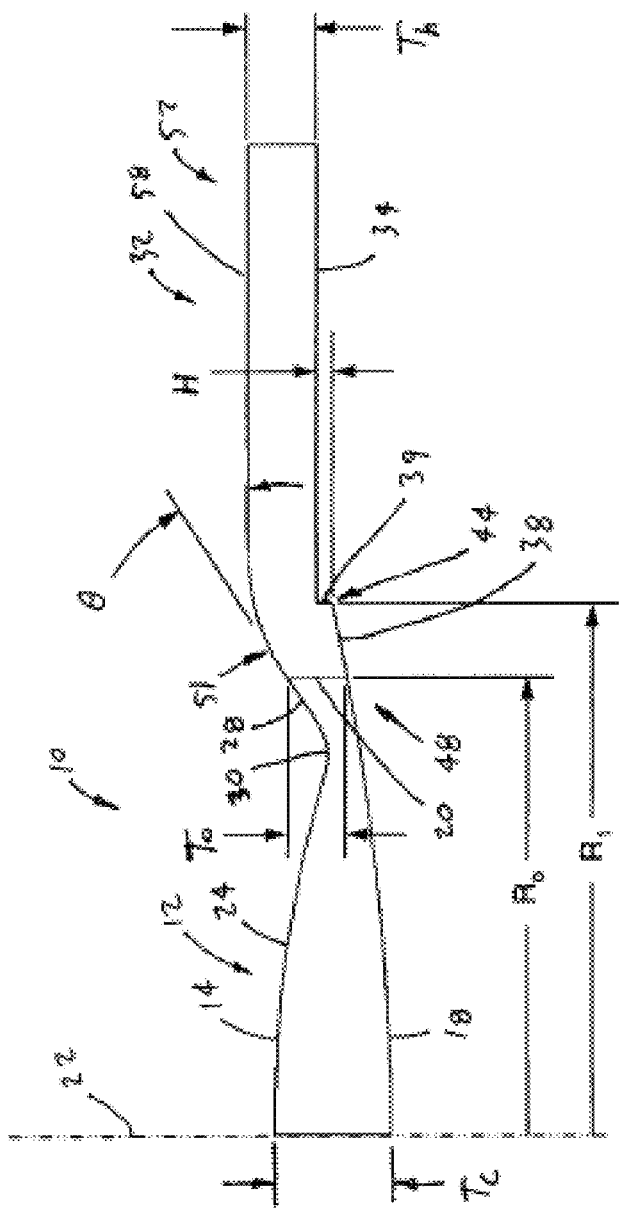
FIG. 3 is a side view of a portion of the intraocular lens shown in FIG. 1.

One embodiment of an intraocular lens suitable for use in connection with the present invention is shown in FIGS. 1-3.

As illustrated in FIGS. 1-3, an intraocular lens 10, which is preferably foldable, comprises an optic body 11 including an optical zone 12 and a peripheral zone 13 entirely surrounding the optical zone 12. The optic body 11 has an anterior face 14, a substantially opposing posterior face 18, an optic edge 20, and an optical axis 22. The anterior face 14 comprises a central face 24, a peripheral face 28, and a recessed annular face 30 therebetween that is disposed posterior to the peripheral face 28. The intraocular lens 10 further comprises at least one haptic 32 that is integrally formed with the peripheral zone 13. The haptic 32 comprises a distal posterior face 34, a proximal posterior face 38, and a step edge 39 disposed at a boundary therebetween. The haptic further comprises a side edge 40 disposed between the optic edge 20 and the step edge 39. The proximal posterior face 38 and the posterior face 18 of the optic body 11 form a continuous surface 48. An edge corner 50 is formed by the intersection of the continuous surface 48 with the optic edge 20, the side edge 40, and the step edge 39.

The optic body 11 is preferably generally circular having a radius Ro and is typically constructed of deformable-elastic transparent lens body of crosslinked acrylic material having a tensile strength sufficient to resist deformation after implantation into the eye as by forces exerted by growing tissue around the IOL; a flexibility as measured by elongation at break sufficient to allow the lens body to be readily folded, rolled or otherwise deformed to a low profile condition for implantation through a small incision into the eye; an elastic memory which enables the folded lens body to naturally and at a controlled rate return to its original shape and optical resolution without damaging or otherwise traumatizing eye tissue; and a low-tack surface which will not stick to surgical instruments used to hold and guide the lens body during insertion and positioning within the eye.

In particular, the optic body is a crosslinked acrylic material comprising copolymers of methacrylate and acrylate esters which are relatively hard when cold and relatively soft at body temperature, crosslinked with a diacrylate ester to produce a cross-linked acrylic material having a substantially tack-free surface, a crosslink density between $0.5 \times 10^{-2}$ and $1.5 \times 10^{-2}$ moles per liter, a glass transition temperature in the range of $-30°$ to $25°$ C., a tensile modulus in the range of 1000 to 3000 psi and an elongation at break of between 100 and 300%. Such a lens body is easily folded, rolled or otherwise deformed into a low profile for insertion through a small incision and after insertion will naturally return to its original optical resolution at a slow controlled rate in between 20 and 180 seconds even if the lens body has been deformed to a low profile condition for an extended period of time. The slow return allows the surgeon adequate time to locate the folded IOL in the eye before the lens body returns to its original shape and resolution and insures that the unfolding of the lens will not damage or otherwise traumatize ocular tissue. Furthermore, the optic body of the foregoing material and composition possesses a desired tensile strength to resist deformation in response to forces exerted by tissue growing around the implanted lens body thereby maintaining the desired optical characteristics and resolution of the lens body.

In some embodiments, in the formation of the deformable-elastic acrylic material, the copolymers of methacrylate and acrylate esters are mixed at approximately a 45 to 55 weight percent ratio and the relatively hard methacrylate ester is a fluoroacrylate. The fluoroacrylate functions as a surface energy lowering agent as well as a monomer providing long term stable inertness and tensile strength to the polymer without adversely effecting the pliancy of the resulting material. In this regard, the fluoroacrylate is present in a concentration range by weight of between 5 and 25% and preferably is trifluoro ethyl methacrylate. Also in the preferred formulation of the crosslinked acrylic, the mixture of the copolymers is partially polymerized prior to chemical crosslinking with diacrylate ester in a concentration range of between 0.5 and 3.0 percent by weight. The polymer may incorporate an ultraviolet (UV) light blocking additive, preferably a permanent (chemically bound) ultraviolet (UV) light-blocking additive known in the art, such as 2-(4-benzoyl-3-hydroxyphenoxy) ethyl acrylate.

The resulting crosslinked acrylic material may be molded and formed into lens bodies machined to have the desired optical characteristics and resolution with haptics extending therefrom either integral with or separately attached to the lens body.

In a preferred embodiment, the optic body 11 is made of SENSAR® IOL brand of hydrophobic acrylic IOL material.

Although the crosslinked acrylic material described herein is described primarily for use in an optic body, the crosslinked acrylic material may be used in other applications wherein a change of refractive index is desired.

The optic body 11 material is preferably selected such that the optical zone 12 is optically clear and exhibits biocompatibility in the environment of the eye. Selection parameters for suitable lens materials are well known to those of skill in the art. See, for example, David J. Apple, et al., Intraocular Lenses. Evolution, Design, Complications, and Pathology, (1989) William & Wilkins. Foldable/deformable materials are particularly advantageous since optics made from such deformable materials may be rolled, folded or otherwise deformed and inserted into the eye through a small incision. The lens material before irradiation preferably has a refractive index allowing a relatively thin, and preferably flexible optic section, for example, having a center thickness in the range of about 150 microns to about 1000 microns, depending on the material and the optical power of the optic body 11. For example, in one embodiment, the optic body 11 is made of SENSAR® IOL brand of acrylic material, an optically clear, hydrophobic, acrylic elastomer with an optical power of 20 D. IOLS made of the composition contained in the SENSAR® IOL brand are described in commonly-owned U.S. Pat. No. 4,834,750, which is incorporated here by reference. In such an exemplary embodiment, the optical zone 12 has a center thickness Tc that is preferably in the range of about 0.5 mm or less to about 1.0 mm or more, more preferably between about 0.7 mm and 0.9 mm. The center thickness Tc may vary from these ranges depending on factors such as the lens material and the dioptric power of the optical zone 12. The optic body 11 preferably has a diameter of at least about 4 mm to about 7 mm or more, more preferably about 5 mm to about 6.5 mm or about 6.0 mm. As used herein the term "thickness" generally refers to a dimension of a portion or feature of the intraocular lens 10 as measured substantially along the optical axis 22.

The intraocular lens 10 may comprise any of the various means available in the art for centering or otherwise locating the optical zone 12 within the eye. For example, as illustrated in FIGS. 1-3, the intraocular lens 10 may comprise one or more fixation members or haptics 32. The haptics 32 are preferably integrally made of the same material as the optic body 11 so as to form a one-piece IOL. Alternatively, the haptics 32 may be integrally formed in a common mold with the optic body 11, but be made of a different material than the optic body 11. In other instances, the haptics 32 formed of the same material as the optic body 11, but haptics 32 and the optic body 11 materials have different states, for instance differing amounts of water content or percentage of cross-linked polymer. In yet other embodiments, the haptics may be formed separately from the optic body 11 and attached to the optic body 11 to provide a three-piece configuration. In such configurations, the haptics 32 may comprise any of a variety of materials which exhibit sufficient supporting strength and resilience, and which are substantially biologically inert in the intended in vivo or in-the-eye environment. Suitable materials for this purpose include, for example, polymeric materials such as polypropylene, PMMA, polycarbonates, polyamides, polyimides, polyacrylates, 2-hydroxymethylmethacrylate, poly (vinylidene fluoride), polytetrafluoroethylene and the like; and metals such as stainless steel, platinum, titanium, tantalum, shape-memory alloys, e.g., nitinol, and the like. In other embodiments, the intraocular lens 10 comprises a positioning means that allows the optic body 11 to move along the optical axis 22 or be deformed in response to deformation of the capsular bag and/or in response to the ciliary muscles of the eye.

The optical zone 12 may take any of the forms known in the art. For example the optical zone 12 may be biconvex, plano-convex, plano-concave, meniscus, or the like. The optical power of the optical zone 12 may be either positive or negative. The general profile or shape of the posterior face 18 and the central face 24 of the optic zone 12 may be any used for producing an optic based on refraction of incident light. For instance, the posterior face 18, the central face 24, or both faces 18, 24 may be spherical with an overall radius of curvature that is either positive or negative. Alternatively, the profile or shape of either the posterior face 18, the central face 24, or both faces 18, 24 may be parabolic or any aspheric shape common in the art for reducing aberrations such as spherical aberrations. For example, the posterior face 18 or the central face 24 may be an aspheric surface designed to reduce spherical aberrations based on either an individual cornea or group of corneas as described by Piers et al. in U.S. Pat. No. 6,609,673 and U.S. patent application Ser. Nos. 10/119,954, 10/724,852, herein incorporated by reference. Other aspheric and asymmetric surface profiles of the posterior face 18 or the central face 24 of use within the art are also consistent with embodiments of the intraocular lens 10. The posterior face 18 or the central face 24 may alternatively be configured to provide more than one focus, for example to correct for both near and distant vision as described by Portney in U.S. Pat. No. 4,898,461.

The optical zone 12 may take any of the forms known in the art. For example the optical zone 12 may be biconvex, plano-convex, plano-concave, meniscus, or the like. The optical power of the optical zone 12 may be either positive or negative. The general profile or shape of the posterior face 18 and the central face 24 of the optic zone 12 may be any used for producing an optic based on refraction of incident light. For instance, the posterior face 18, the central face 24, or both faces 18, 24 may be spherical with an overall radius of curvature that is either positive or negative. Alternatively, the profile or shape of either the posterior face 18, the central face 24, or both faces 18, 24 may be parabolic or any aspheric shape common in the art for reducing aberrations such as spherical aberrations. For example, the posterior face 18 or the central face 24 may be an aspheric surface designed to reduce spherical aberrations based on either an individual cornea or group of corneas as described by Piers et al. in U.S. Pat. No. 6,609,673 and U.S. patent application Ser. Nos. 10/119,954, 10/724,852, herein incorporated by reference. Other aspheric and asymmetric surface profiles of the posterior face 18 or the central face 24 of use within the art are also consistent with embodiments of the intraocular lens 10. The posterior face 18 or the central face 24 may alternatively be configured to provide more than one focus, for example to correct for both near and distant vision as described by Portney in U.S. Pat. No. 4,898,461.

At least portions of the posterior face 18, the central face 24, or both faces 18, 24 of the optical zone 12 may comprise one or more optical phase plates. In such embodiments, the total optical power of the optical zone 12 is a combination of the refractive power of the posterior face 18 and the central face 24, and the optical power of the one or more diffraction orders produced by the one or more phase plates. The one or more phase plates may be either a monofocal phase plate providing one dominant diffraction order or a multifocal phase plate, such as a bifocal phase plate, for providing, for instance, simultaneous near and distant vision. Other types of phase plates may also be used. For example, the phase plate may be based on a change in the refractive index of the material used to form the optical zone 12.

The total optical power of the optical zone 12 is preferably within a range of at least about +2 Diopters to about +50 Diopters or more, more preferably within a range of about +5 Diopters to about +40 Diopters, and most preferably a range of about +5 Diopters to about +30 Diopters. The total optical power may be either positive or negative, for instance within a range of about −15 Diopters or less to about +15 Diopters or more, or within a range of about −10 Diopters to about +10 Diopters. Other ranges of refractive optical power may be preferred, depending on the particular application and type of intraocular lens to be used.

In certain embodiments, the haptics 32 are characterized by a haptic thickness Th that is equal to a distance, as measured along the optical axis 22, between the distal posterior face 34 of the haptic 32 and the substantially opposing anterior face 58. Preferably, the haptic thickness Th is greater than or approximately equal to an optic edge thickness To, as measured along the optical axis 22. The thicknesses Th and To may be selected based on the particular material from which the intraocular lens 10 is made, the amount of rigidity desired, the optical power of the lens 10, and other such factors. In one embodiment, at least one of the haptic thickness The optic edge thickness To, is between at least about 0.4 mm to about 0.5 mm or more.

As a result of the step edge 39, the distal posterior face 34 of each haptics 32 has an anterior offset relative to the proximal posterior face 38. In certain embodiments, the step edge 39 has a thickness H that is much less than the optic edge thickness To. For example, the step edge thickness H is about 0.1 mm and the optic edge thickness To is between about 0.4 mm or less and about 0.5 mm or more. Alternatively, in other embodiments, the step edge thickness H is greater than or approximately equal to the optic edge thickness To. The step edge thickness H may be selected based on various design parameters, including, the particular material from which the intraocular lens 10 is made, the amount of rigidity desired in the haptics 32, and other such factors. Preferably, step edge thickness H is selected sufficiently large so that the integrity of the contact of the edge corner 50 with the posterior capsule of the eye is maintained so as to help avoid PCO.

In certain embodiments, at least a portion of the step edge 39 is a straight line and is substantially disposed at a radius R1 from the optical axis 22. Alternatively or additionally, at least a portion of the step edge 39 may be arcuate in shape. The radius R1 is advantageously greater than the radius Ro of the optic edge 20 so that a proximal portion of the haptic 32 forms a buttress 51 that is preferably thicker than a distal portion 52 of the haptic 32 and the edge thickness To. The buttress 51 of each haptic 32 provides greater haptic rigidity in the vicinity of the peripheral zone 13, resulting in a biasing force that biases the distal portion 52 of the haptic 32 away from the optical zone 12. The biasing force away from the optical zone 12 can favorably act to reduce the tendency of the haptics 32 to stick to the optical zone 12. Such sticking problems have been noted with certain one-piece IOL materials that are both soft and tacky. Another potential benefit of the step edge 39 is that the thickness of the distal portion 52 of each haptic 32 Th may be fabricated to be less than the thickness of the buttress 51, thus reducing the total volume of the intraocular lens 10 and permitting a smaller incision in the eye to be used during surgery. The greater haptic rigidity in the vicinity of the peripheral zone 13 of the optic body 11 also results in a radial force for centering the intraocular lens 10 within the eye and provides an axial force, as explained below herein. The axial force pushes the edge corner 50 that surrounds the posterior face 18 against the posterior capsule of the eye to help prevent PCO. Disposing the step edge 39 at a radius R1 that is greater than Ro provides yet another potential advantage. The greater rigidity provided by the buttress 51 permits the creation of a flex point Wf near the peripheral zone 13 that allows the haptic 32 to flex in a plane perpendicular to the optical axis 22 while maintaining overall rigidity in the vicinity of $W_f$. As illustrated in FIG. 2, the width of the haptic 32 in the vicinity of the flex point $W_f$ is less than the haptic thickness in the vicinity of the flex point $W_f$. Thus, the haptic 32 may flex more in a plane perpendicular to the optical axis 22 than in a plane parallel to the optical axis 22.

In certain embodiments, the peripheral zone 13 is substantially formed by the peripheral face 28, the optic edge 20, and the peripheral portion of the posterior face 18. As illustrated in FIG. 1, the peripheral zone 13 and the buttress 51 form generally rigid structures, the rigidity of the buttress 51 being due, at least in part, to the favorable location of the step edge 39 at the radius R1, on the haptic 32. The location of step edge 39 at a radius R1>R0 in combination with the rigidity of the peripheral zone 13 allows the central face 24 to be recessed such that the recessed annular face 30 of the peripheral zone 13 is posterior to the peripheral face 28. This recessed configuration of the central face 24, compared to an optic not having the recessed annular face 30, advantageously reduces the total volume of the intraocular lens 10 by reducing the overall thickness of the optical zone 12. Alternatively, the central face 24 is not recessed, thus increasing the overall rigidity of the intraocular lens 10, but also increasing the total volume of the lens.

As illustrated in FIG. 3, in certain embodiments, the distal posterior face 34 of each haptic 32 is perpendicular to the optical axis 22. In other embodiments, the haptic 32 further comprises an anterior face 58 that is also substantially perpendicular to the optical axis. In such embodiments, the step edge 39 produces an offset relationship between the distal portion 52 of the haptics 32 and the peripheral zone 13. This offset relationship may be favorably used to convert the radial force of the ciliary muscles of the eye on the haptics 32 into an axial force that biases or pushes the posterior face 18 of the optic body 11 in a posterior direction along the optical axis 22 and against the posterior capsule of the eye. This is accomplished without the need for angled haptics, which can be more difficult and/or expensive to manufacture than when the distal posterior face 34, the anterior face 58, or both the distal posterior face 34 and the anterior face 58 are manufactured substantially perpendicular to the optical axis. Alternatively, the haptics 32 may be manufactured such that the distal posterior face 34 and/or the anterior face 58 are disposed at an angle relative to a plane perpendicular to the optical axis 22. This configuration may be used to increase the amount of posterior bias or force on the posterior face 18 of the optic body 11 against the posterior capsule. In such configuration the angle is preferably between about 2 degrees or less and at least about 12 degrees.

In many embodiments, the index of refraction of the acrylic material is achieved by irradiation of the acrylic material with a suitable light source. In many embodiments, the light source is a pulsed laser.

Figure 4:
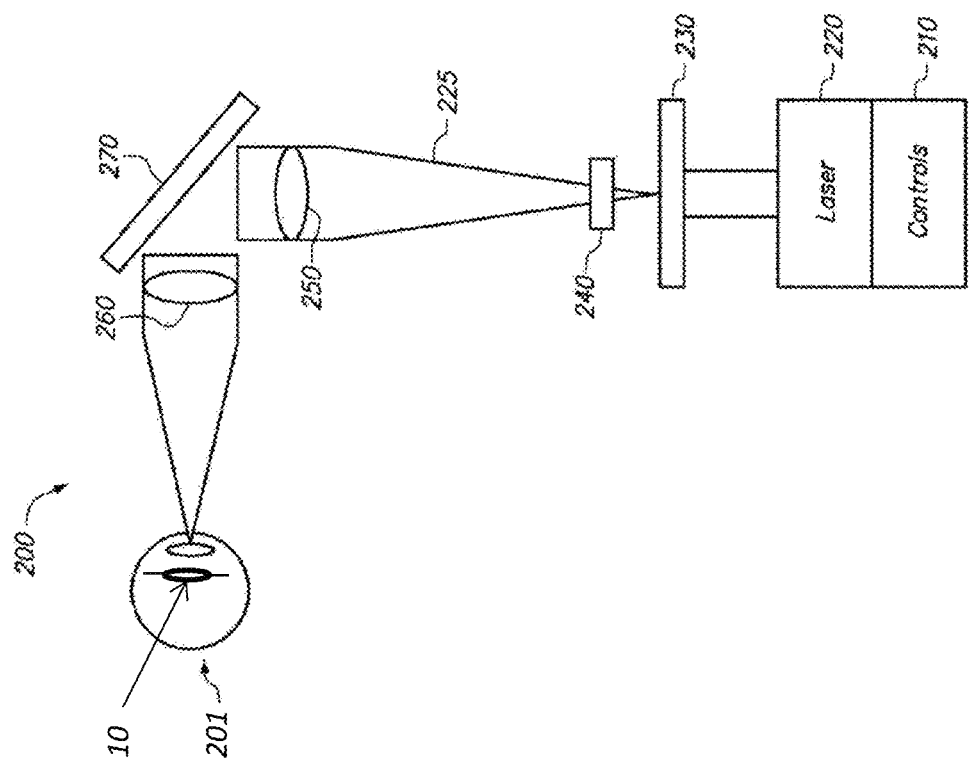
FIG. 4 is an illustration of a system for modifying the refractive index of an acrylic material according to many embodiments of the present invention.

The present invention can be implemented by a system 200 that projects or scans an optical beam into a patient's eye 201 containing the optic 10, such as the system shown in FIG. 4. The system 200 includes control electronics 210, a light source 220, an attenuator 230, a beam expander 240, focusing lens' 250, 260 and reflection means 270. Control electronics 210 may be a computer, microcontroller, etc. Scanning may be achieved by using one or more moveable optical elements (e.g. lenses 250, 260, reflection means 270) which also may be controlled by control electronics 210, via input and output devices (not shown). Another means of scanning might be enabled by an electro optical deflector device (single axis or dual axis) in the optical path. Although FIG. 4 shows the optical beam directed to a patient's eye, it should be understood that the intraocular lens may be irradiated before placement into the patient's eye in order to customize a refractive property of the intraocular lens.

During operation, the light source 220 generates an optical beam 225 whereby reflection means 270 may be tilted to deviate the optical beam 225 and direct beam 225 towards the patient's eye 201 and particularly into the crosslinked acrylic polymer in order to alter the refractive index of said polymeric acrylic. Focusing lens' 250, 260 can be used to focus the optical beam 225 into the patient's eye 201. The positioning and character of optical beam 225 and/or the scan pattern it forms on the eye 201 may be further controlled by use of an input device such as a joystick, or any other appropriate user input device.

Although not shown in FIG. 4, the laser system 200 preferably also includes imaging and visualization sub-systems, such as and without limitation, an optical coherence tomography (OCT) system, a video monitoring system, etc. These sub-systems are used to provide images of and to locate the various anatomical structures of the eye as well as the IOL, which can assist in performance of the various methods described later in this disclosure. Many types of imaging and visualization sub-systems are known in the art and their detailed descriptions are omitted here. For example, commonly owned U.S. Pat. No. 8,845,625, which is incorporated herein by reference in its entirely, discloses in its FIGS. 1-4 and accompanying descriptions in the specification, an ophthalmic laser surgical system that includes an ultrafast laser source, a beam delivery optical system including scanning devices, an OCT system, an imaging system for viewing an image of the eye, an aim beam system, and related control system.

The selected light source is not particularly limited so long as the emitted radiation is capable of modifying the refractive index of the crosslinked acrylic material in the manner desired. In many embodiments, the selected light source is a laser, and more particularly a pulsed laser source.

In many embodiments, the light source is a 320 nm to 800 nm pulsed laser source. In many embodiments, the light source 220 is a 320 nm to 800 nm laser source such as an tunable femtosecond laser system or it may be a Nd:YAG laser source operating at the 2nd harmonic wavelength, 532 nm, or 3rd harmonic wavelength, 355 nm. Other options are frequency double or tripled femtosecond laser sources which emissions fall in this spectral band. One limit of the suitable wavelengths is the transmission of the cornea. The transmission of the cornea at 355 nm is about 85% and starts to strongly drop off at 320 nm (50% transmission) to 300 nm with about 2% transmission whereas the lens absorption is approximately 99%. Also, for older people, light scattering of the cornea is minimal while light scattering of the lens has considerably increased (cataract). Important to the wavelength selection is that the crosslinked acrylic polymer shows multi-photon (two or three photo for example) absorption at the used laser wavelength and the laser wavelength itself is not linearly absorbed by the material.

In operation, the light of the light source is focused and is scanned in the crosslinked acrylic polymer in order to effect a change of the refractive index in a volume of the crosslinked acrylic polymer. The shape and volume of the volume whose refractive index is changed is determined by the change in the refractive property of the intraocular lens that is desired. The shape of the volume effected by the irradiation with the light source is not particularly limited. For instance, the volume may be lens shaped, biconvex, plano-convex, plano-concave, meniscus, or the like, disc shaped, parabolic or their wave-stepped Fresnel-type combination thereof—or in any other 3-dimensional shape suitable to cause the desired change in refractive property of the intraocular lens.

Where a pulsed laser source is used, the focused pulsed laser source is swept in an array of laser pulses having a predetermined spot size and spot spacing. The array of laser pulses may be repeated in the same pattern a predetermined number of times such that substantially the same locations within the crosslinked acrylic polymer are irradiated a predetermined number of times. These array repeats may be accomplished by sweeping the laser source such that all the predetermined repeats are irradiated at a first laser position before laser source is moved to a second position in the crosslinked acrylic polymer. These repeats can also just be shifted to a slightly different depth in order to affect relative untreated volume but with the same pattern. Single lay depth difference may be in the order of 1 to 200 um more preferred 2 to 15 um. Alternatively, the array repeats may be accomplished by completing a first sweep of the array with the pulsed laser beam and depositing one pulse at each array position and then repeating the array sweep for subsequent repeat. Preferably, the crosslinked acrylic polymer absorbs at least a portion of the laser radiation.

The pulse energy of laser pulses is generally between 0.01 µJ and 50 µJ. In many embodiments, the pulse energy will be between 0.05 µJ and 20 µJ, or more precisely, between 0.1 µJ and 0.7 µJ, or between 0.05 µJ and 1 µJ.

A pulse repetition rate of the laser pulses is generally between 1 kHz and 10 MHz. In many embodiments, the pulse repetition rate is between 100 kHz to 600 kHz, or between 1 KHz to 80 KHz.

Spot sizes of the laser pulses are generally smaller than 20 µm. In many embodiments, the spot size is preferably smaller than 15 µm, typically 0.5 µm to 3 µm. In some embodiments, the spot size is in the range of 10 µm to 15 µm.

Figure 10A:
FIGS. 10A and 10B show that irradiation of a crosslinked acrylic material irradiated with a nanosecond laser can cause an index change comparable to a femtosecond laser.
Figure 10B:
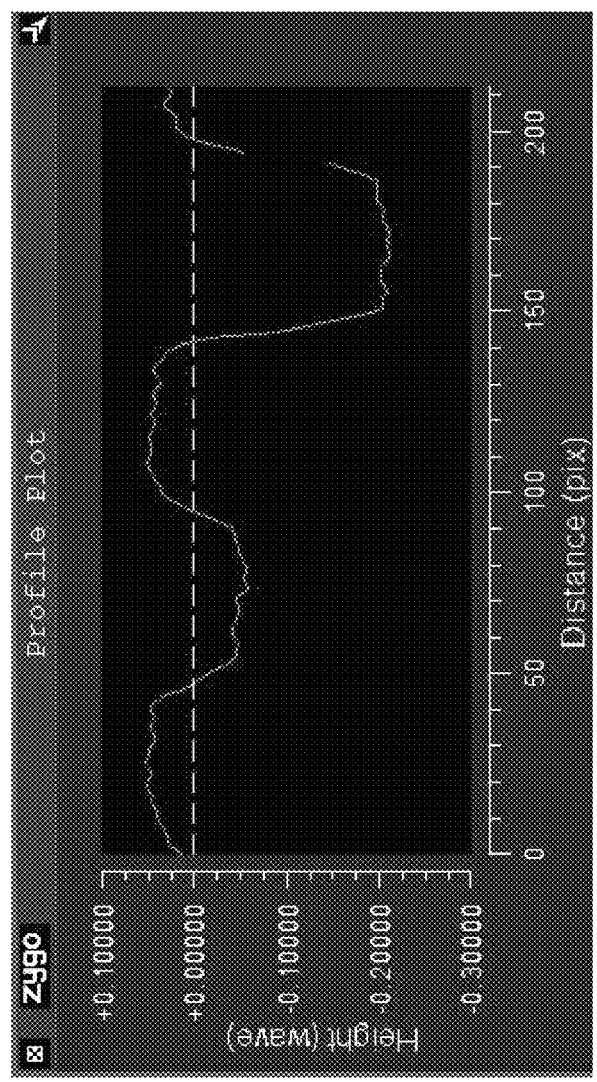

When a pulsed laser source is used, a pulse duration of the laser pulses is generally between 0.1 ps and 10 ns. For purposes of this application, femtosecond laser pulses are generally referred to as pulsed durations from 100 fs to 500 fs, and nanosecond laser pulses are defined as laser pulses from 0.5 ns to 10 ns. FIGS. 10A and 10B show that irradiation of a crosslinked acrylic material irradiated with a nanosecond laser can cause an index change comparable to a femtosecond laser. FIG. 10A is an image of the index change in a crosslinked acrylic material irradiated with a 0.6 ns pulse laser, with a repetition rate of 30 kHz, a pulse energy of 6.6 µJ, a spot size 1.5 µm, with 1, 2, 4, 8 and 16 irradiation repeats. This has approximately the same index change as when the crosslinked acrylic material is irradiated with a 0.6 ps pulse laser, with a repetition rate of 30 kHz, a pulse energy of 1 µJ, a spot size 1.5 µm, with 1, 2, 4, 8 and 10 irradiation repeats. Both cases result in a maximum change of the index of refraction of 0.25 lambda.

A numerical aperture should be selected that preferably provides for the focal spot of the laser beam to be scanned over a scan range of 6 mm to 10 mm in a direction lateral to a Z-axis that is aligned with the laser beam. The NA of the system should be less than 0.6, preferably less than 0.5 and more preferably in a range of 0.01 to 0.4, typically between 0.03 and 0.3. In some specific embodiments, the NA is 0.15. In a femtosecond laser system, the NA is 0.02 to 0.09 with wavelength being 705 nm.

Figure 5:
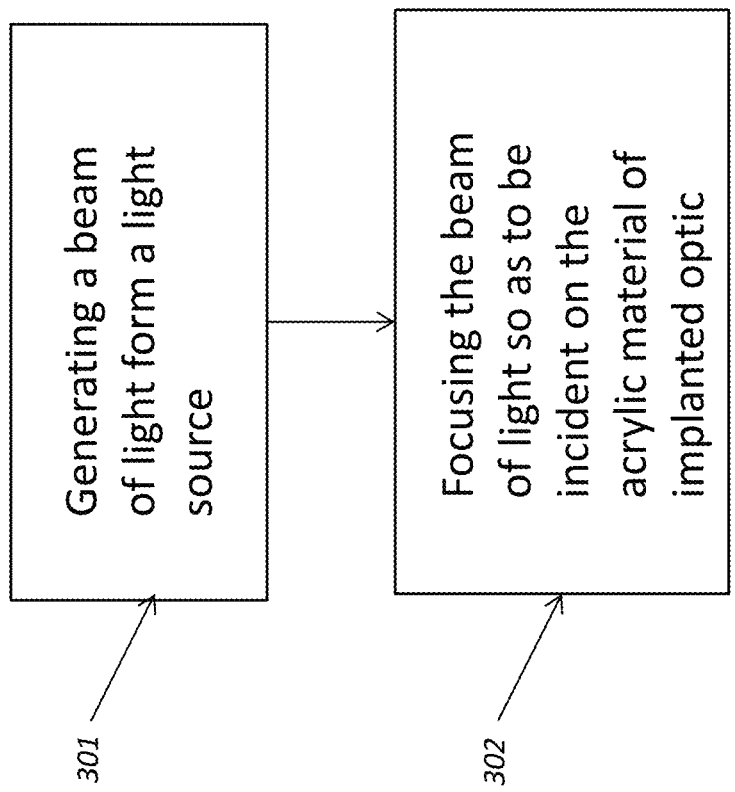
FIG. 5 is a flowchart of a method in accordance with an embodiment of modifying a refractive index of an acrylic material according to the present invention.

FIG. 5 shows a flowchart of a method in accordance with an embodiment of the present invention. A first step 301 involves generating a beam of light from a 320 nm to 800 nm laser system. A next step 302 involves translating and focusing the beam of light within the eye in a controlled fashion so as to be incident on the acrylic material inside said eye in order to modify the refractive index of said material to modify the refractive state.

Irradiation with the light beam as described herein results in a change in refractive index of the cross-linked acrylic polymer, thereby causing the predetermined change in the refractive property of the intraocular lens. Applicants have determined that the crosslinked acrylic polymers exhibit both positive and negative changes in the refractive index of the material after irradiation with the laser light source. That is, the crosslinked acrylic materials exhibit a first change in the refractive index that is negative during a first time period after irradiation and a second change in the refractive index that is positive in a second time period after irradiation. The first time period may precede the second time period or may occur after the second time period. That is, in the crosslinked acrylic material, there is both a positive and negative index change after irradiation, and both the negative and positive changes in the index of refraction contribute to the resulting (i.e. final) index of refraction of the irradiated material.

It should be emphasized that different IOL materials respond to laser irradiation differently in terms of the sign and magnitude of the refractive index change or the time course of the change. The behavior of each material may be understood through experimentation. Some specific examples are described below, and it should be noted that the principle and methods described below may be applied to other IOL materials with suitable modifications.

Without being limited by theory, one effect of the laser irradiation is to change the hydrophobicity of the acrylic material. As a result, water is expelled from the area in or around the area that has been irradiated, which causes or may cause a positive change in the refractive index. Another effect of the laser irradiation is to cause local heating portion of the crosslinked acrylic polymer irradiated with the laser pulses, which causes or may cause a negative index change in the material. Also, also changes the hydrophobicity, which causes a positive index change. The index change typically is proportional to total energy.

This feature of having both a positive and negative index change is illustrated in FIGS. 6 and 7. FIG. 6A shows an image of a change in index of refraction of an acrylic material irradiated with a femtosecond material at 1 hour after exposure as a function of pulse energy and number of repeat pulse exposures. Pulse energy is increased from 0.1 µJ to 0.5 µJ for 1-5 repeats of the laser pulses. A blue color indicates a positive index change. A red color indicates a negative index change. FIG. 6B represents the same sample 1 day after treatment. Note that the outlines of the squares on the upper right stays after diffusion process and the sign of the index modification has changed from 1 hour to 1 day.

Figures 7A, 7B:
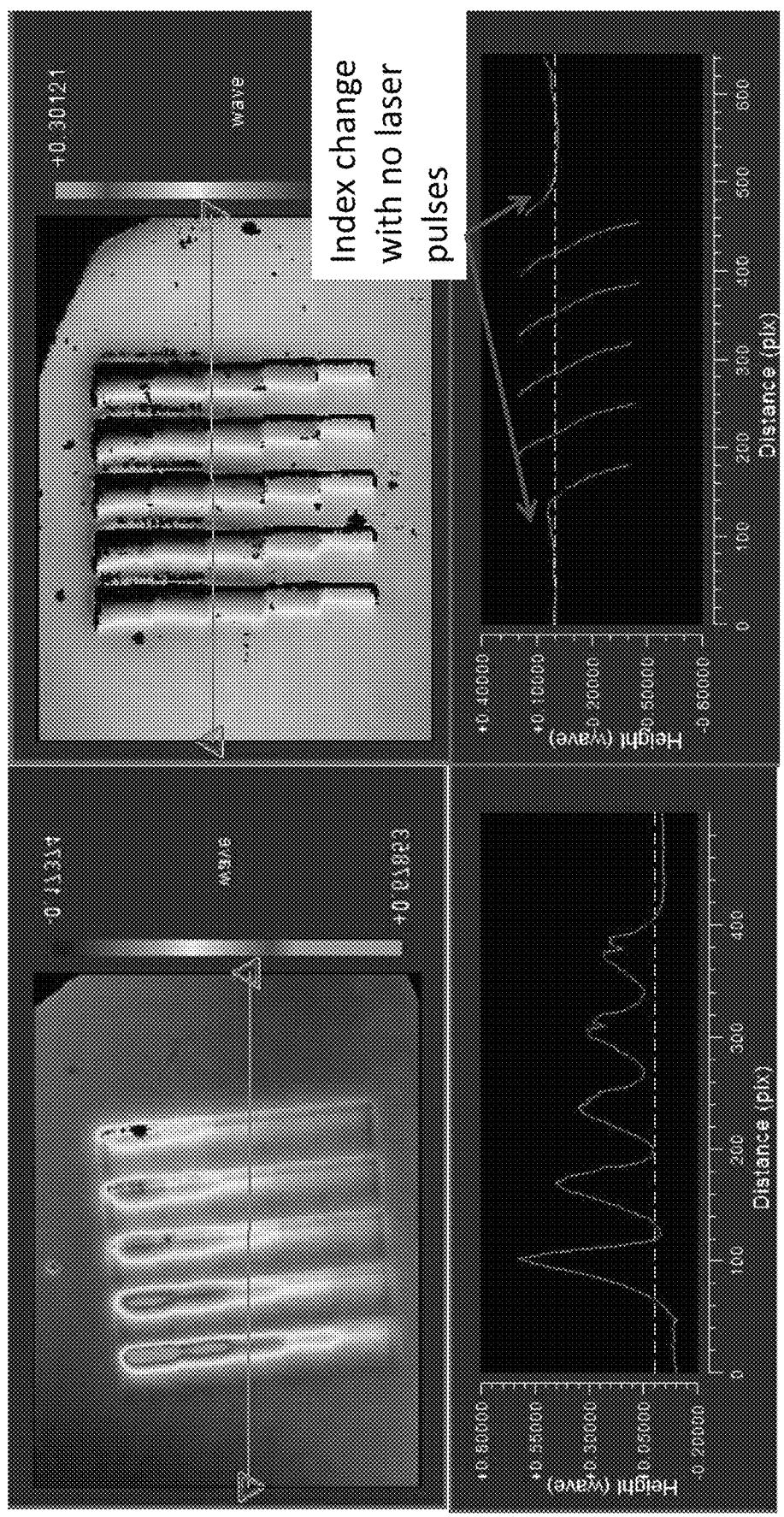
FIG. 7A shows an image of a change in index of refraction of an acrylic material irradiated with a femtosecond material at 1 hour after exposure as a function of pulse energy and number of repeat pulse exposures. The repetition rate is 30 kHz, with a 12 µm beam waist, 1 µm spot spacing, and a pulse energy of 2-2.5-3-3.5-4 µJ, 5 repeats. A red color indicates a negative index change. A blue color indicates a positive index change.
FIG. 7B represents the same sample 1 day after treatment. As visible on the cross-sections the sign of the index change has changed between the two different time points.

FIG. 7A shows an image of a change in index of refraction of an acrylic material irradiated with a femtosecond material at 1 hour after exposure as a function of pulse energy and number of repeat pulse exposures. The repetition rate is 30 kHz, with a 12 µm beam waist, 1 µm spot spacing, and a pulse energy of 2-2.5-3-3.5-4 µJ, 5 repeats. A red color indicates a negative index change. A blue color indicates a positive index change. FIG. 7B represents the same sample 1 day after treatment. As visible on the cross-sections the sign of the index change has changed between the two different time points.

Following completion of the positive and negative index changes, the irradiated volume of the crosslinked acrylic material reaches a final equilibrium state characterized by an index of refraction that is different from the index of refraction of the crosslinked acrylic polymer in its pre-irradiated state and different from the index of refraction of the of the crosslinked acrylic material that has not been irradiated. That is, the change in refractive index relative to the pre-irradiation refractive index (or relative to the index of the refraction of the non-irradiated portion of the lens) in the crosslinked acrylic polymer is proportion to a total energy of the irradiation with the light source at each location. In preferred embodiments, the change in refractive index relative to the pre-irradiation refractive index (or relative to the index of the refraction of the non-irradiated portion of the lens) in the crosslinked acrylic polymer is linearly proportional to a total energy of the irradiation with the light source at each location.

This feature is shown, for instance, in FIGS. 8 and 9. FIG. 8A is a graph of index of refraction vs pulse energy (micro Joules) for a crosslinked acrylic material irradiated with a femtosecond laser with 4 repeat laser pulses at 1 and 3 days post irradiation. Note that the index of refraction change of the acrylic material is linear with total energy at 3 days post irradiation. FIG. 8B is a graph of laser pulse energy (micro Joules) vs. index of refraction for a crosslinked acrylic material irradiated with a femtosecond laser with 8 repeat laser pulses at 1 and 3 days post irradiation. Note that the index of refraction change of the acrylic material is linear with total energy at 3 days post irradiation. FIG. 8C is a graph of index of refraction vs. pattern repeats for an acrylic material irradiated with a femtosecond laser at 3 days post irradiation. Note that the index of refraction change of the acrylic material is generally linear with the number of pattern repeats at 3 days post irradiation.

Figure 9A:
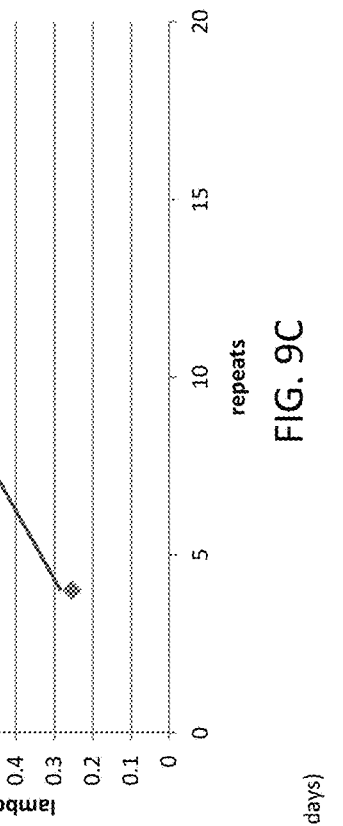
FIG. 9A is a graph of laser pulse energy vs. index of refraction for a crosslinked acrylic material in water at 37° C. irradiated with a femtosecond laser with 16 repeat laser pulses at 1 and 3 days post irradiation. Note that the index of refraction change of the acrylic material is linear with total energy at 3 days post irradiation.
Figure 9B:
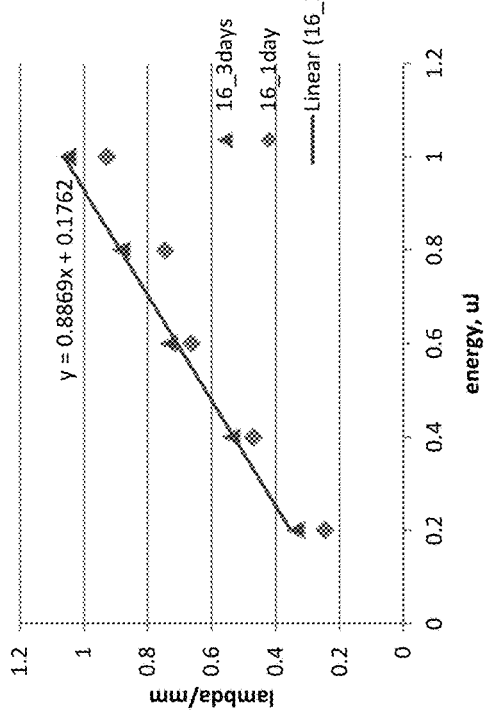
FIG. 9B is a graph of laser pulse energy vs. index of refraction for a crosslinked acrylic material in water at 37° C. irradiated with a femtosecond laser with 8 repeat laser pulses at 1 and 3 days post irradiation. Note that the index of refraction change of the acrylic material is linear with total energy at 3 days post irradiation.
Figure 9C:
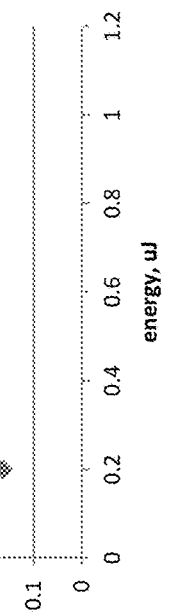
FIG. 9C is a graph of pattern repeats vs. index of refraction for an acrylic material irradiated with a femtosecond laser at 3 days post irradiation. Note that the index of refraction change of the acrylic material is generally linear with the number of array repeats at 3 days post irradiation.

FIG. 9A is a graph of laser pulse energy vs. index of refraction for a crosslinked acrylic material in water at 37° C. irradiated with a femtosecond laser with 16 repeat laser pulses at 1 and 3 days post irradiation. Note that the index of refraction change of the acrylic material is linear with total energy at 3 days post irradiation. FIG. 9B is a graph of laser pulse energy vs. index of refraction for a crosslinked acrylic material in water at 37° C. irradiated with a femtosecond laser with 8 repeat laser pulses at 1 and 3 days post irradiation. Note that the index of refraction change of the acrylic material is linear with total energy at 3 days post irradiation. FIG. 9C is a graph of pattern repeats vs. index of refraction for an acrylic material irradiated with a femtosecond laser at 3 days post irradiation. Note that the index of refraction change of the acrylic material is generally linear with the number of array repeats at 3 days post irradiation.

It should be noted that for some other IOL materials, the change in refractive index at each location due to laser irradiation may change in a non-linear manner with respect to the total energy of the irradiation. The behavior of each IOL material may be understood through experimentation.

U.S. Pat. Nos. 4,834,750 and 7,615,073 and U.S. Patent Publication 2015/0335477 are incorporated herein by reference in their entirety.

Refractive Index Modification Through Localized Heating Using Multi-Photon Absorption Modification of refractive index of the intraocular lens may be achieved by directly altering the chemical bonds of the crosslinked acrylic material of the lens through multi-photon absorption. To directly alter the chemical bonds, photon energy of >5 eV is needed, which requires two- or three-photon absorption in the visible wavelength range. One problem with this approach is that most IOL materials are specifically made to be very resistant to chemical changes, as they are designed and manufacture to be inert and fully cured prior to implantation and should not react to anything once implanted. In the embodiments described below, instead of changing the chemical bonds to alter the chemical structure of the IOL material, a pulsed laser beam is used to locally alter the refractive index of the IOL material by means of localized heating. Further, the wavelength and power density of the pulse laser beam are selected to induce multiphoton absorption of the laser light. In other words, the laser energy is absorbed by the IOL material through multiphoton absorption, and majority of the absorbed energy is released as heat to heat the IOL material locally to alter its refractive index locally.

In some embodiments, the laser light used for refractive index modification is in either the UV/blue spectral range (e.g. 400-450 nm) or the far red/NIR spectral range (e.g. 650-800 nm), and multi-photon absorption allows for photons in these spectral ranges to be absorbed by the IOL material with relatively high absorption rate. These two wavelength ranges are preferred as they are in ranges of low human retinal sensitivity, compared to the green spectral range which has the highest sensitivity. Low spectral sensitivity therefore allows good patient compliance.

Figure 11:
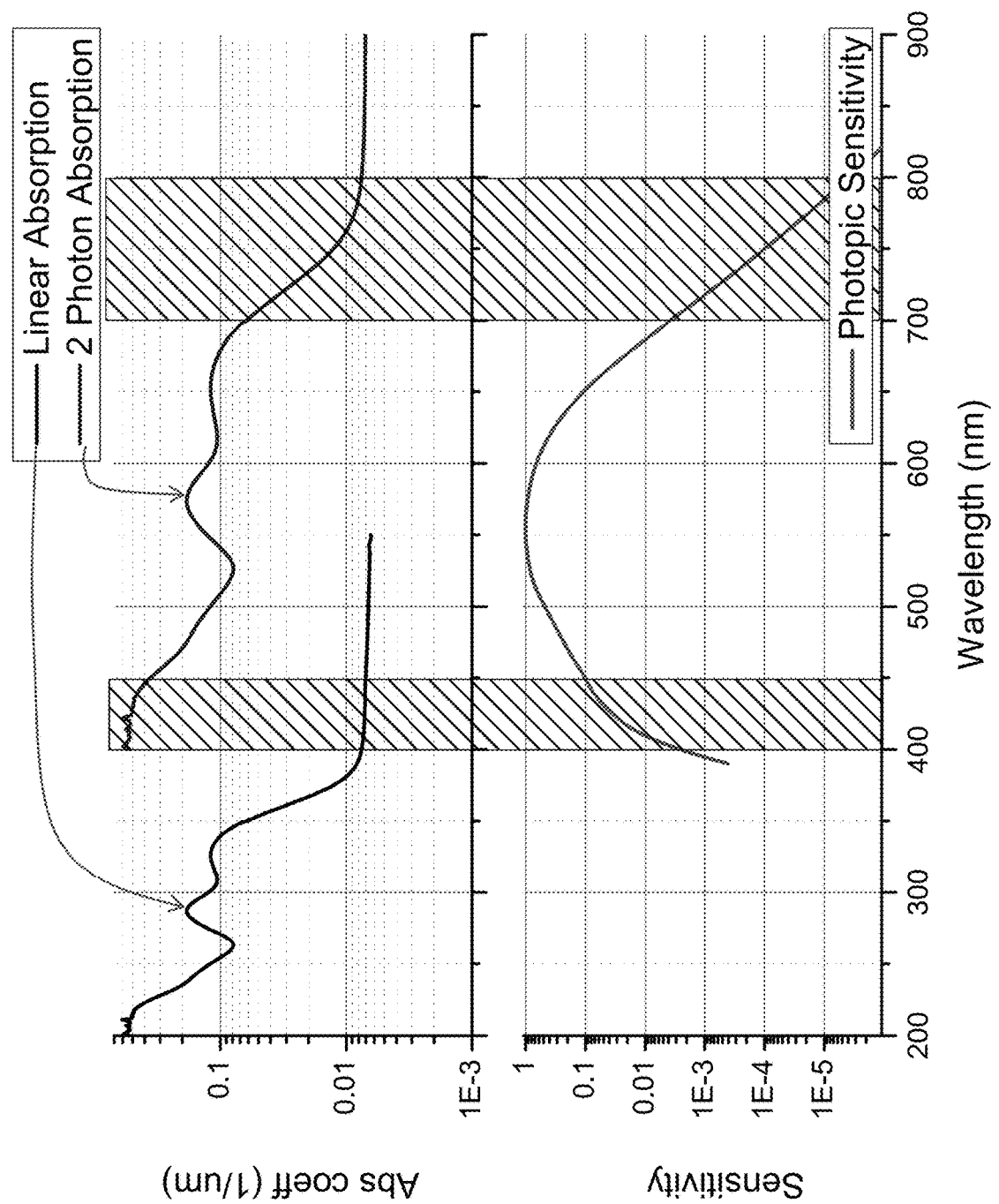
FIG. 11 illustrates the absorption of a thin layer of an acrylic material, showing both the linear (single photon) absorption coefficient and the two-photon absorption coefficient, as well as the photopic sensitivity curve of the human eye and high-lightened spectral areas in which a significant two photo absorption can be achieved along with minimal photopic sensitivity to the human eye.

The upper panel of FIG. 11 illustrates the absorption of a thin sample of exemplary acrylic material (the SENSAR® IOL brand acrylic), showing both the linear (single photon) absorption coefficient and the two-photon absorption coefficient (both in units of per micrometer layer thickness). The linear absorption coefficient has strong absorption in the UV spectral range, up to about 365 nm, and then becomes transparent starting at about 390 nm. The two-photon absorption spectrum, which corresponds to the linear absorption curve but at doubled wavelength, reaches the NIR range. The lower panel of FIG. 11 illustrates the photopic sensitivity curve of the human eye. It can be seen that in the two spectral ranges mentioned above, namely the UV/blue range (e.g. 400-450 nm) and the far red/NIR range (e.g. 650-800 nm), the photopic sensitivity of the eye is relatively low, while the two-photon absorption is still sufficiently high. This make the two-photon absorption treatment process applicable without damaging the retina of the patient with the treatment light. This ensures good patient cooperation during the exposure. If one uses light at the peak spectral sensitivity one can expect adverse reactions of patients as unused light is transmitted to the retina In particular, in the far red and NIR spectral range, the light does not cause photochemical reaction on the retina, so only thermal safety limit for the retina needs to be met.

The direct linear absorption in the blue/UV spectral range may also be used. In this range, however, the photochemical effect on the retina may be a concern, and the treatment must meet the retinal safety limit (which is a very low dosage). Additionally, the limited corneal transmission in this spectral range due to increased light scattering in the aged cornea of the target population may also reduce the effectiveness of such an approach.

While one specific example of IOL material is given above, different IOL materials with different single photon UV absorption characteristic may change the usable spectral range due to the specific cut-off wavelengths of their UV/blue absorbance. For yellow dyed IOL materials, this range can significantly shift into the red spectral region or into the near IR range. Further, specific resonant dye absorbers, which have narrow absorption peaks tailored to specific laser wavelengths, may be introduced into the IOL material. If the bandwidth is narrow enough, it may be used even in the visible spectral range as only little energy is absorbed. Dyes which are specifically only sensitive for two-photon absorption may also be used.

Figure 12:
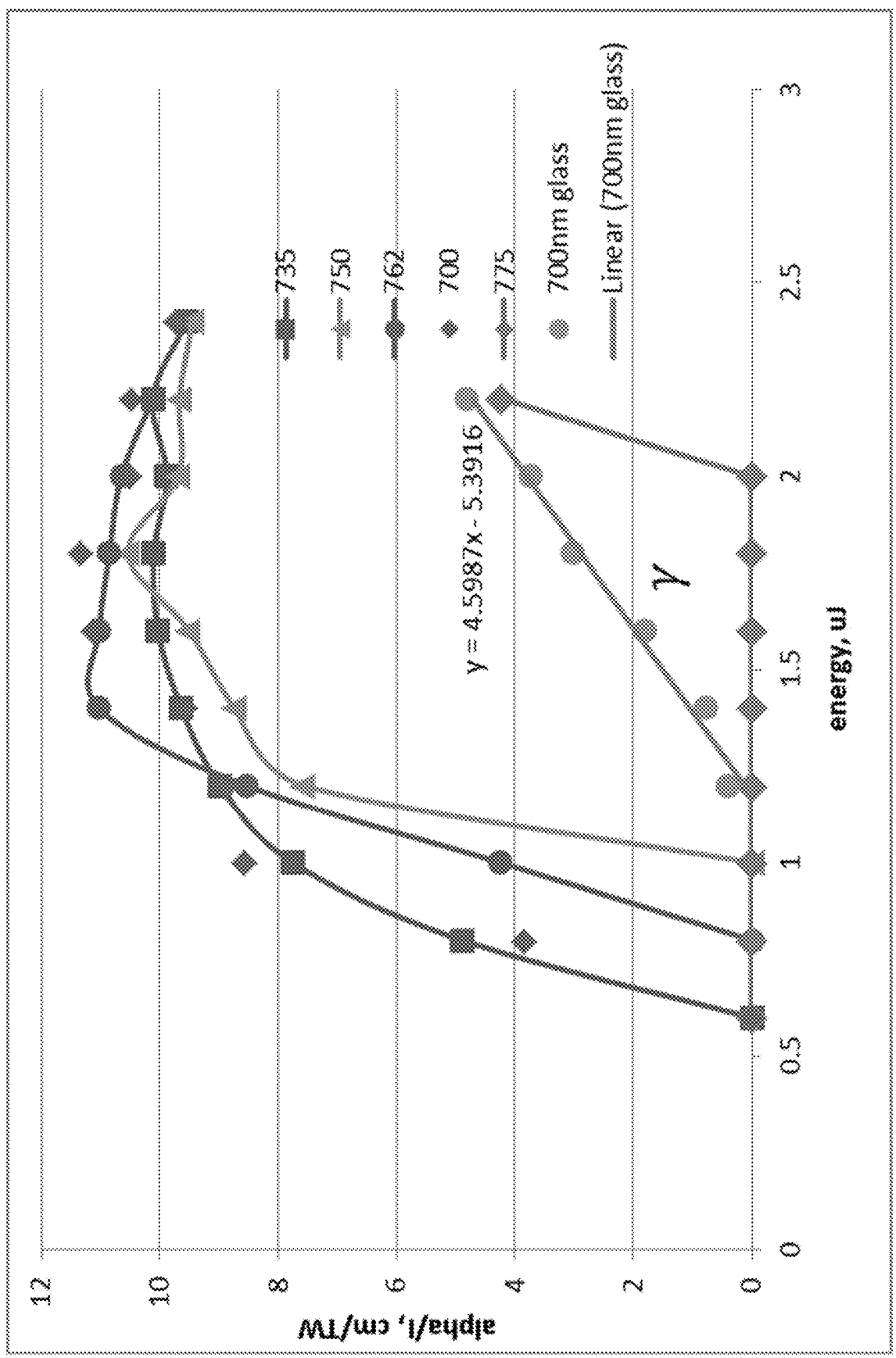
FIG. 12 shows experimentally obtained two-photon absorption coefficient for the acrylic material as a function of pulse energy applied to the sample for different laser wavelengths as well as glass as a reference sample for 3 photon absorption.

The two-photon absorption coefficient of the IOL material may be derived experimentally. FIG. 12 shows experimentally obtained two-photon absorption coefficient ($\alpha/I$) for the SENSAR® IOL brand of acrylic material as a function of pulse energy applied to the sample, for different laser wavelengths in the NIR range. As shown in FIG. 12, at wavelengths of 700 nm, 735 nm, 750 nm, and 762 nm, the absorption coefficient starts to increase rapidly at certain pulse energy and then reaches a plateau, indicating a stable two-photon absorption behavior. As a reference, the two-photon absorption coefficient of glass at 700 nm is also shown, but in the pulse energy range shown, it rises linearly with energy but never reaches a plateau with a stable 2 photon absorption, which indicates a three-photon absorption behavior.

The two-photon absorption coefficient as a function of the pulse energy may be obtained by measuring the transmission rate of the light through the sample as a function of pulse energy, then fitting two constants (threshold and coefficient) to the measured transmission rate data. In one particular example, the equation used for the curve fitting is as follows:

$$T = \frac{\pi w_0^2}{2BP_m} \log\left[1 + \frac{2P_m B}{\pi w_0^2}\right]$$

Where $P_m$ is the incident power on the material, $w_0$ is the Gaussian beam waist radius, and:

$$B = z_R \beta \left[\text{Arctan}\left(\frac{z - z_0}{zR}\right) - \text{Arctan}\left(\frac{z_m - z_0}{zR}\right)\right]$$

Where zR is the Rayleigh range, $z_0$ is the beam waist location, z is the location of bottom of material, $z_m$ is location of the top of the material, and β is the TPA coefficient which has two fit parameters $P_{th}$ and $P_{width}$ as given below:

$$\beta(P) = \beta_o \left(\frac{1}{2} + \frac{1}{\pi}\text{Arctan}\left(\frac{P_m - P_{th}}{P_{width}}\right)\right)$$

Figure 13A:
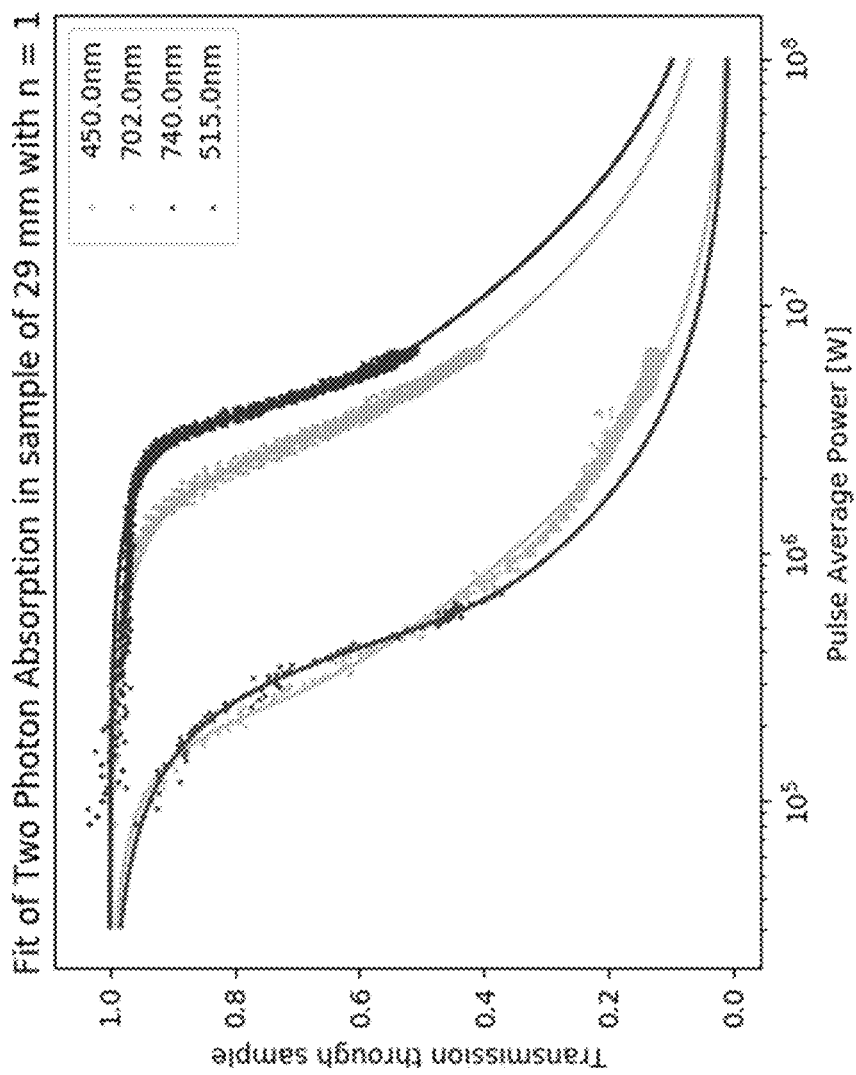
FIG. 13A shows measured transmission data over laser pulse average power (over pulse duration) using the acrylic material at four wavelengths and the corresponding curve fitting matching to a two photon absorption of the incident laser light.
Figure 13B:
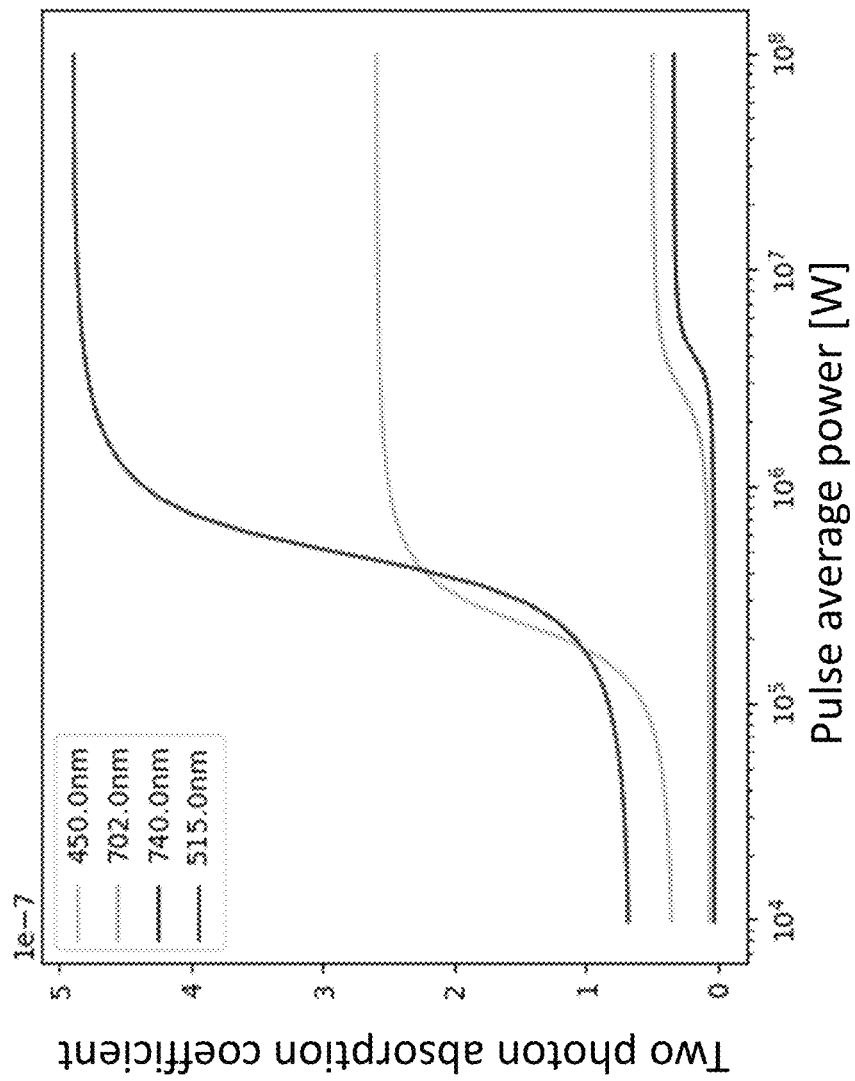
FIG. 13B shows the calculated two-photon absorption coefficient as a function of pulse energy at the wavelengths using the measured data in FIG. 13A.

FIG. 13A shows measured transmission data using the SENSAR® IOL brand of acrylic material at four wavelengths, 450 nm, 515 nm, 702 nm and 740 nm, and the corresponding curve fitting matching to a two photon absorption of the incident laser light, and FIG. 13B shows the calculated two-photon absorption coefficient as a function of pulse energy at these wavelengths. Note that in FIGS. 13A and 13B, the pulse energy has been converted to pulse average power.

As mentioned earlier, certain chromophores may be added to the IOL material to absorb other laser wavelengths to induce two-photon absorption and the associated heating. For example, a UV-blocking IOL material, containing a UV filter, such as the TECNIS® OptiBlue IOL, which has relatively high absorption for blue light, can be altered with a 780 nm short pulsed laser as it still has significant absorption at 390 nm, while the non-UV-blocking IOL material, such as the SENSAR® IOL is already in the transition zone for this wavelength. It is also possible to use wavelength specific absorbers for 515 nm light which may then allow the use of 1030 nm lasers light which are non-visible for the patients. The TECNIS® OptiBlue IOL is described in commonly-owned U.S. Pat. No. 7,278,737, which is incorporated herein by reference.

Figure 14B:
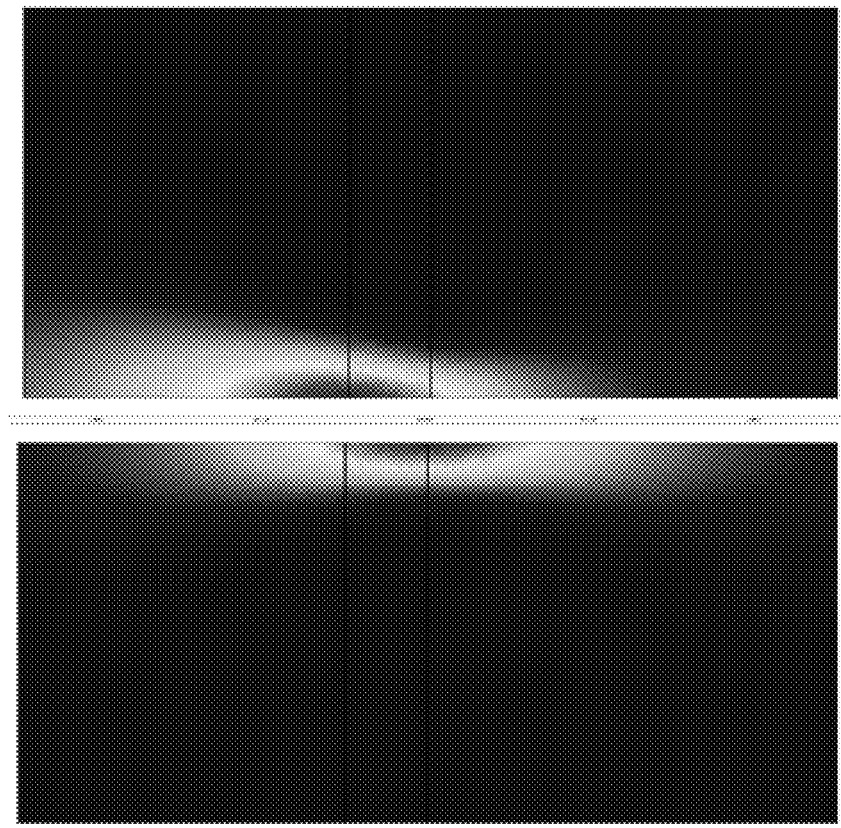
Figure 14A:
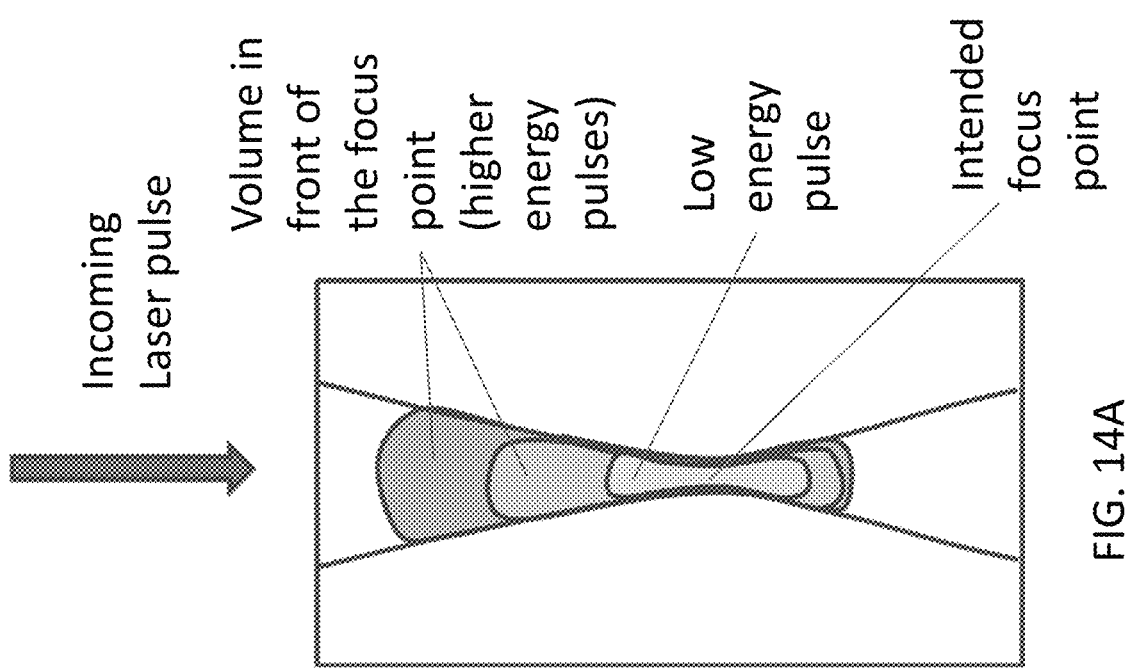

One effect of two-photon absorption is the self-limitation of the laser effect on the material at the focus spot. Such self-limitation is caused by the light of the laser pulse being absorbed and even depleted shortly before it reaches the intended focus spot due to the onset of two photon absorption in the volume in front of the focus, as the power density becomes sufficiently high in that volume due to focusing and exceeds the threshold of two-photon absorption. FIG. 14A schematically illustrates the effect that at higher pulse energies, the laser light is absorbed further up the focal volume, i.e. closer to the incident laser light. FIG. 14B shows numerical simulations of the absorbed energy distribution of the laser light within the SENSAR® IOL material using the measured two-photon absorption coefficient, showing the simulated energy absorption at 20 nJ (left) and 2 uJ (right). It can be seen that the spatial distribution of pulse energy absorption is shifted towards the incident laser (from the top) and very little energy is deposited in the much smaller intended focal volume. This effect has also been confirmed experimentally using cross-sectional phase contrast imaging and fluorescence imaging. FIG. 14C is a cross-sectional phase contrast image showing vertical lines of index changes generated in a SENSAR® IOL material at different laser pulse energies but uniform focal depth. FIG. 14D are fluorescence images of the cross-section of the material showing the autofluorescence from the material during laser irradiations, which is indicative of the amount of energy absorbed. Both figures show that the areas of index change or light absorption for lower energy pulses are deeper in the material while the those for higher pulse energy shifted upwards, closer to the incoming laser pulses.

Figure 15:
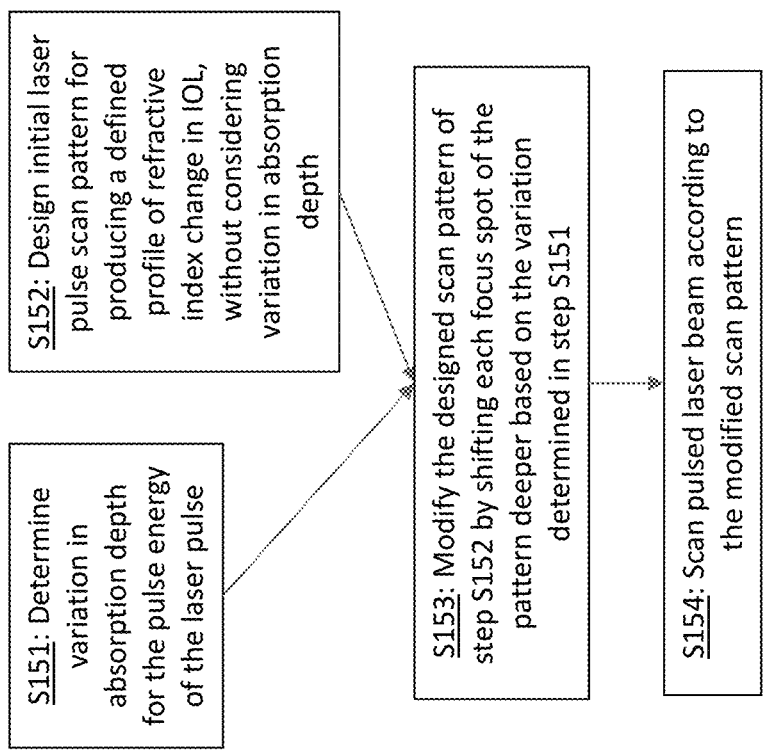
FIG. 15 is a flow chart illustrating a refractive index modification method according to an embodiment of the present invention. Correction of the intensity dependent focus is applied.

This self-limitation effect can prevent plasma formation and the associated damage of the IOL material due to high power density at the intended focus spot. Thus, higher pulse energy may be used without damaging the IOL material. In other words, this effect intrinsically increases the dynamic range of the desired effect without causing optical breakdown in the laser focus and damage of the sample. On the other hand, the variable depth effect, i.e. the change in absorption depth with pulse energy, means that the laser pulse irradiation pattern should be designed to take this effect into account, so that the actual absorption depth occurs at intended depths. In practice (see FIG. 15), for a given lens material and given laser system parameters (e.g. the focal distance and the numerical aperture of the system), the shift in absorption depth due to multiphoton absorption at given pulse energies can be obtained (step S151), for example, by numerical simulation or experimental observation as mentioned above. Then, an initial laser pulse scan pattern, which has been designed to produce a defined refractive index modification profile in the IOL (step S152), is modified by moving the designed depth of each focus spot to a deeper location based on the shift obtained in step S151 (step S153). When the pulsed laser beam is scanned according to the modified scan pattern (step S154), the resulting refractive index modification pattern will be the same as the defined pattern designed in step S152.

Figure 23:
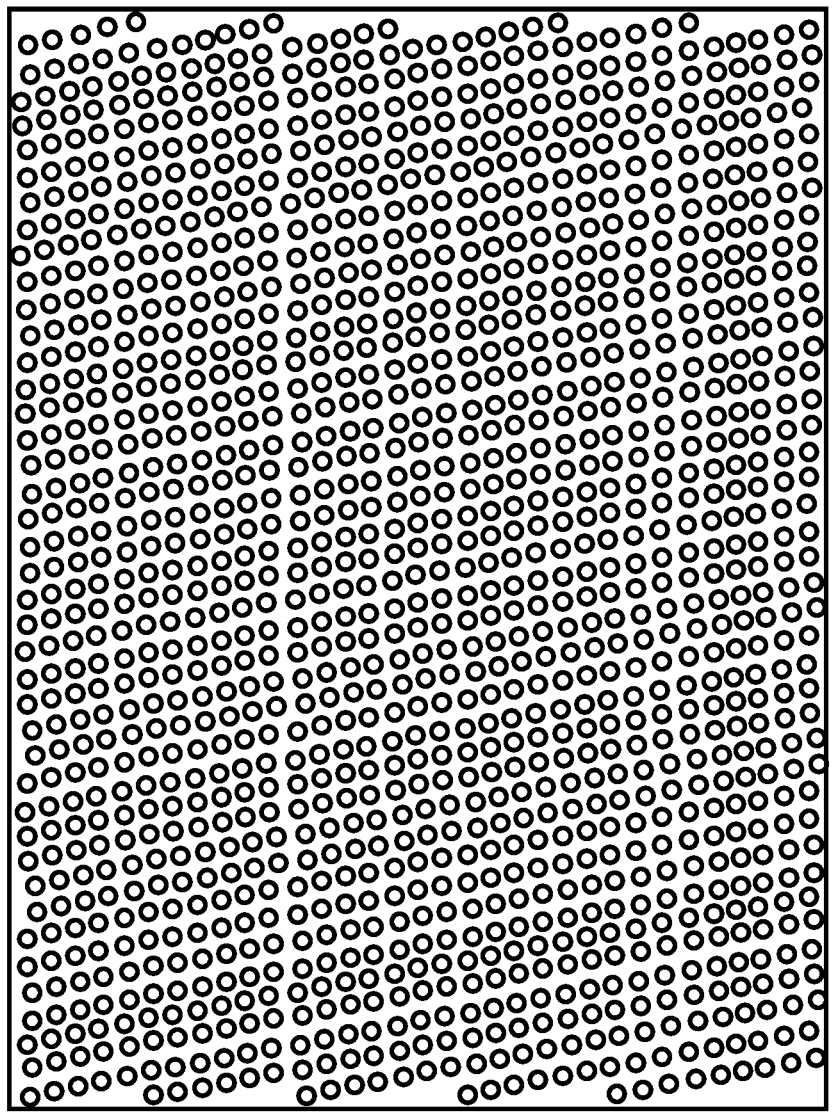
FIG. 23 shows ring-shaped focus spots formed by a vortex beam according to an embodiment of the present invention.

In addition to a Gaussian beam profile, other beam profiles may be used, such as a top hat shaped beam (where the light intensity profile is flat in a center region), a vortex beam (where the light intensity peaks at radial positions away from the beam center), etc. For example, spatial pulse shaping using vortex beams can be utilized to optimize the induced laser efficacy while increasing the threshold for material damage as the threshold for plasma formation is hard to reach under these conditions. A vortex beam can form a ring shaped focus spot in the material, which can result in a more spatially even distribution of energy as compared to a beam profile that peaks at the beam center. FIG. 23 shows ring-shaped focus spots formed by a vortex beam in a SENSAR® IOL material; the pulse energy was 1.5 uJ and the spot spacing was 15 μm.

Another factor that generates a self-limiting effect during laser processing of the IOL material is thermal lensing. Thermal lensing in an optical medium is induced by temperature gradient in the medium, which changes the refractive index of the material and causes bending of the light.

The effect is temporary, and disappears when the temperature gradient disappears due to heat diffusion. When processing the IOL material using a laser beam, when the pulse repetition rate is sufficiently high and the focus spots of successive pulses are located sufficiently close to each other in space, the focusing of the subsequent pulses may be affected by the thermal lensing effect due to the heat generated by previous laser pulses. The induced thermal lensing may limit the formation of a good laser focus spot, i.e., it may defocus the laser beam.

The magnitude of the thermal lensing effect for a given material may be estimated by numerical simulation. In methods described below that take thermal lensing effect into consideration, simulation results may be used to determine, for a given set of parameters, whether the effect of thermal lensing is desirable/undesirable or acceptable/unacceptable, or to optimize various parameters, depending on practical requirements.

Generally speaking, if defocusing of the laser beam is to be avoided, the successive laser spots in a scan pattern should be placed outside of the thermal impact zone of the previous pulses. On the other hand, the defocusing reduces the energy density at the focus spot, which may beneficially avoid plasma formation at the focus spot and the resulting damage of the lens material. As a result of the defocusing, a much higher average power of the laser beam may be used without causing plasma formation and damage to the IOL material. Thus, in some embodiments, the laser parameters (such as pulse energy, pulse repetition rate, etc.) and the scan pattern (such as the spot spacing between adjacent laser spots) are designed such that a thermal lensing effect is induced in the IOL material to cause subsequent laser pulses to be defocused. When such a technique is used, a laser beam of higher average power may be used without damaging the IOL material.

Another method that takes thermal lensing effect into consideration is interlaced scan patterns. The thermal lensing effect is such that placing one pulse or line too close to a previous one may reduce the efficiency of the index change. By creating a pattern that increases the time given for heat to dissipate before the laser returns, efficiency can be increases. For example, if multiple laser scan layers 1, 2, 3, 4, 5, 6, 7, and 8 are to be formed in that spatial order (e.g. from deep to shallow, or from shallow to deep), then instead of forming the layers in a time order of layers 1, 2, 3, 4, 5, 6, 7, and 8, the layers may be formed in an interlaced time order such as layers 1, 3, 5, 7, 2, 4, 6, and 8; or 1, 5, 2, 6, 3, 7, 4, and 8; or some other interlaced scheme. Similarly, for the scan lines within a scan layer or the spots within a scan line, the lines or spots may be formed in the interlaced manner. More generally, an interlaced pattern here refers to a laser pulse scan pattern where layers (or lines, or spots) that are immediately adjacent each other in the spatial order are not immediately adjacent each other in the time order. Numerical simulations mentioned earlier may be used to determine what spatial spacing is needed for a given laser pulse repetition rate to avoid unacceptable thermal lensing, so as to design the interlaced scan pattern accordingly. By generating interlaced scan patterns, one can generate significant index changes with high efficiency without damaging the lens material.

In another scanning method that utilizes the thermal lensing effect, pre-pulses that have much lower energy than the refractive index modifying pulses (e.g., 1:10 to 1:100 of the energy of the refractive index modifying pulses) are delivered to the IOL material at suitable locations to heat the IOL materials to form a transient thermal lens, which will slightly defocus the subsequent refractive index modifying pulses that immediately follow the pre-pulses. The delay between pre-pulse and pulse should be about 100 ps to 100 ns. One practical benefit of this technique is to deal with the fact that the patient's corneal transparency may deviate spot to spot significantly. At places where the corneal transparency is high, the pulse energy that reaches the IOL material will be stronger; at these places, thermal lensing effect in the IOL will also be stronger, causing the laser focus spot to be more defocused, thereby reducing the power density at the focus spot. Thus, the thermal lensing effect can mitigate the undesirable effect of variation in the patient's corneal transparency. Another practical benefit of thermal lensing is that it allows for the use of optical systems with relatively low numerical aperture. In-vivo refractive index modification requires relatively low (<0.2) numerical aperture (NA). Small NA is beneficial for cost of the system and efficacy of the refractive index modification. NA less than 0.01 can become dangerous, however, because of the small beam diameter on the retina. Using the pre-pulsing technique, or simply taking advantage of the previous treatment pulses, to create thermal lens on the way to the retina, the beam can be defocused, and the light spot on the retina is correspondingly larger.

Figure 16:
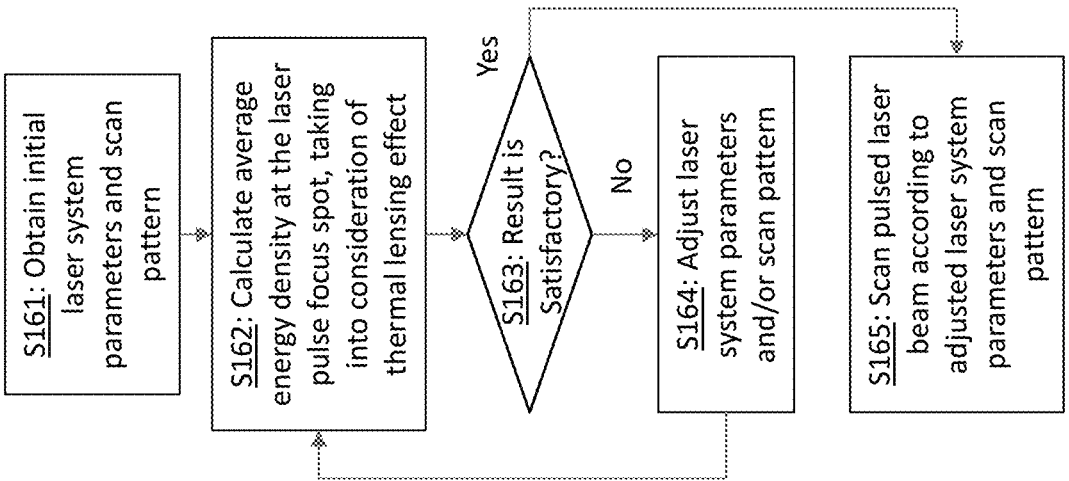
FIG. 16 is a flow chart illustrating a refractive index modification method according to an embodiment of the present invention considering thermal lensing of the acrylic material.

In practice (see FIG. 16), based on the refractive index modification profile to be accomplished in a given IOL material, the laser system parameters may be selected and the scan pattern determined initially without consideration of the thermal lensing effect (step S161). Then, using the initial parameters and scan pattern, the transient refractive index change due to thermal lensing effect, as well as its effect on the actual focus spot size of the laser pulses within the IOL and hence the average energy density (per unit area) at the focus spot, can be determined, for example, by numerical simulation (step S162). The laser system parameters and/or the scan pattern may be adjusted (step S164), and the simulation may be re-performed for the adjusted parameters (step S162), until a satisfactory result is achieved ("Yes" in step S163). For example, the adjustment may increase the laser pulse energy if the calculation indicates that the actual energy density at the focus spot, after taking into consideration of thermal lensing effect, is still sufficiently below the safety limitation. In another example of step S164, the laser pulse scan pattern is adjusted to use an interlaced pattern described earlier. The pulsed laser beam is then scanned using the adjusted laser system parameters and scan pattern (step S165).

To obtain high refractive index differences within an IOL material, multiple modified layers may be spatially stacked on top of each other, and the refractive index changes of the multiple modified layers add to each other along the optical path in a generally linear relationship. Similar effects can be generated by use of a laser optical system with a relatively low NA, which forms a longer (in the depth direction) focus spot that can generate the full desired refractive index change of the IOL within one modified layer.

Figure 17A:
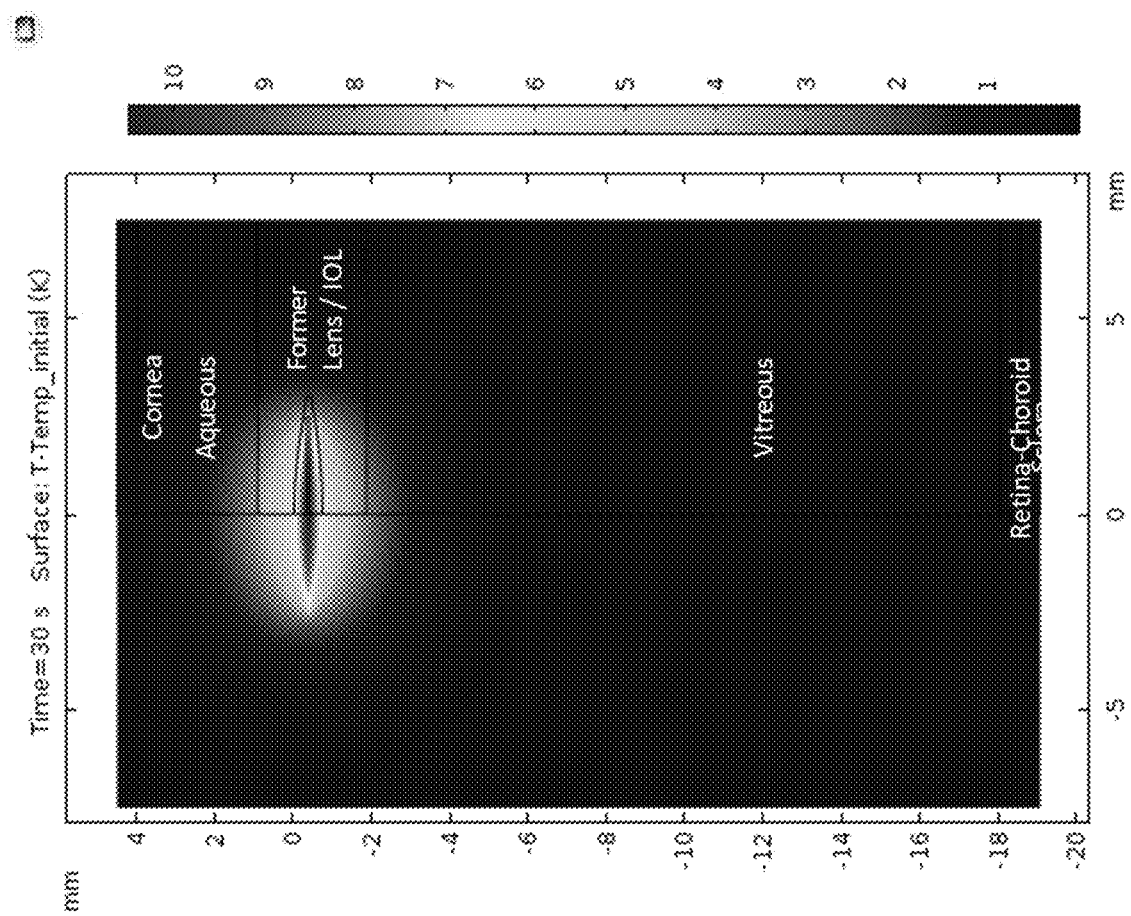
FIG. 17A shows the thermal FEM modeling of an exemplary IOL with an exemplary uniform laser volume heating due to laser exposure and light absorption inside the lens.
Figure 17B:
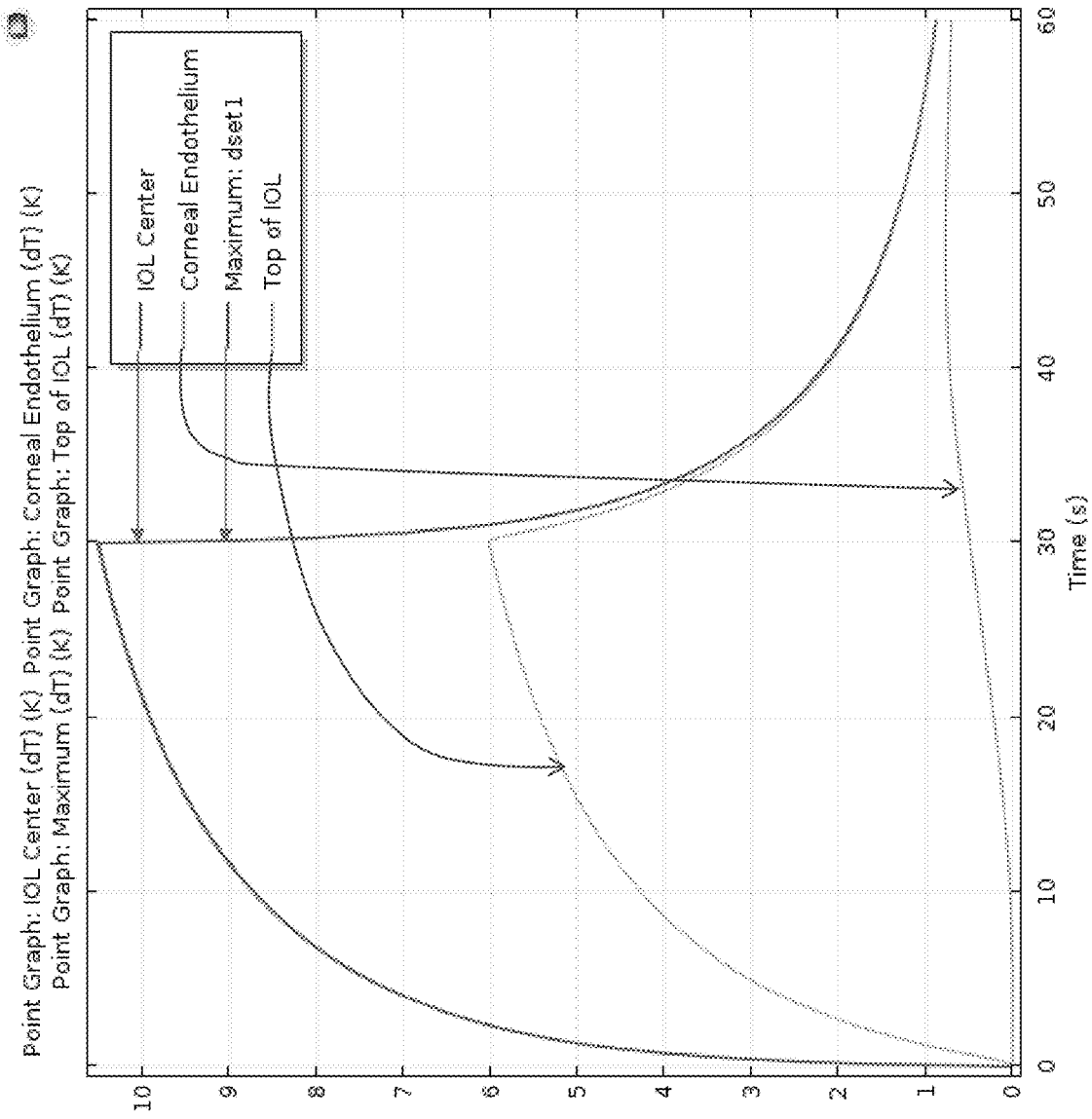
FIG. 17B shows the time course of selected points within the volume of the eye after laser pulse irradiation in the modeling of FIG. 17A.

To produce desired refractive index change over a volume of the lens, refractive index change produced by single laser pulses are combined by scanning the pulsed laser beam ("writing") according to a pattern. Scanning a pattern of laser pulses in the lens loads the lens with thermal energy, as significant amount of energy is absorbed in the IOL as described earlier. The thermal load in the lens need to be carefully managed. Numerical simulation, such as thermal FEM modeling, may be used to calculate expected temperature distribution produced by a pulsed laser scan pattern. FIG. 17A shows the thermal FEM modeling of an IOL with uniform laser volume heating of 100 mW for 30 seconds and of a 100 um thick layer within the IOL. The represented color graph is the temperature distribution at the end of the 30 sec heating cycle. FIG. 17B shows the time course of selected points within the volume of the eye, including the center of the heating source (max temperature), the corneal endothelium, and the top surface of the IOL. Such simulations may be used to determine the thermal load distribution of given laser scan patterns, and to correspondingly adjust the laser parameters and scan pattern so as to ensure that the thermal load distribution in the eye is within levels safe for human exposure.

Figures 18A, 18B:
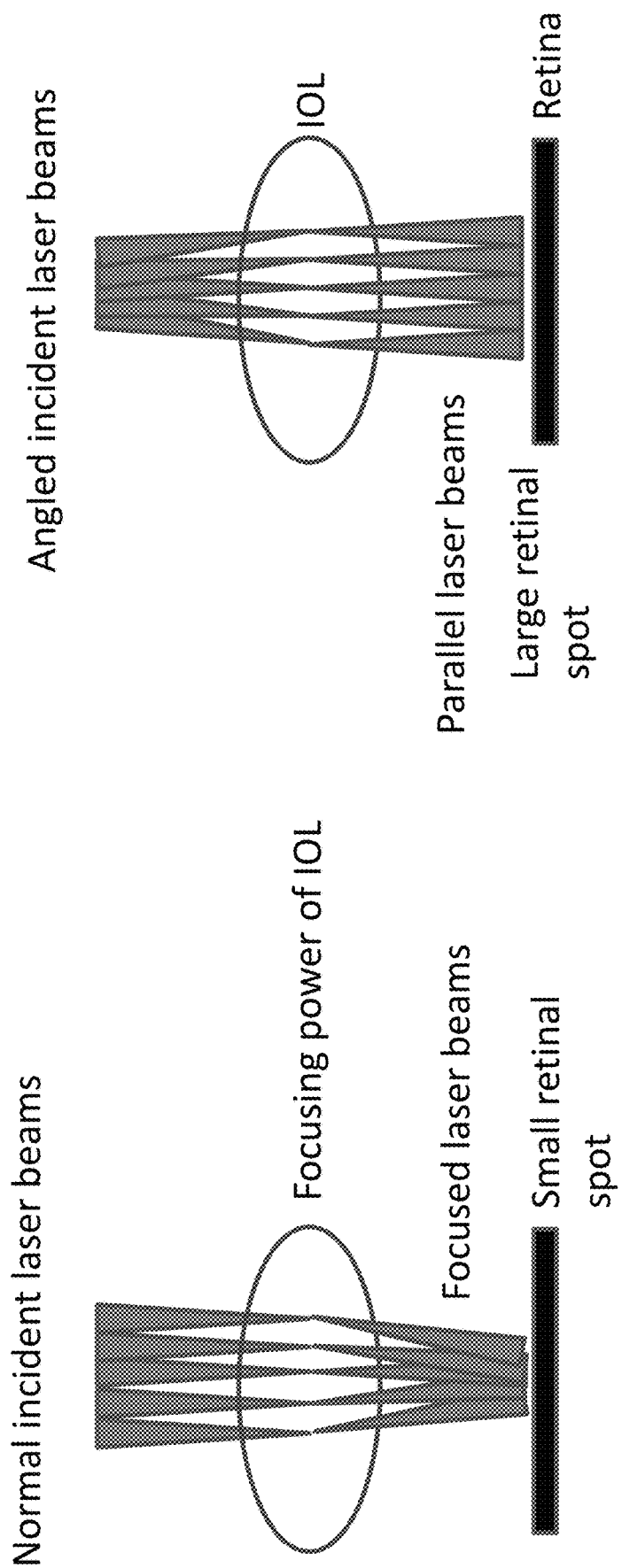
FIGS. 18A and 18B illustrates pre-compensation of laser beam direction to ensure a sufficiently large light distribution area on the retina in order to reduce light intensity on the retina, according to an embodiment of the present invention.

For safe human applications, the optical geometry of the laser system may be designed to ensure a sufficiently large light distribution area on the retina in order to reduce light intensity there. Because the laser beam is focused inside the IOL and then passes through the IOL to reach the retina, and because the IOL has a positive optical power, the refractive power of the IOL will cause the beam spot on the retina to be more concentrated as compared to when the IOL is not present. To ensure that safety limits for the retina are satisfied, the beam concentration effect of the IOL may be counteract by pre-compensating the input laser beam. In one embodiment, the pre-compensation is achieved by directing the laser beam to the IOL at an angled direction that is non-parallel to the optical axis. As a result, higher laser power may be used to process the IOL without exceeding the safety limit for the retina, which improves the laser processing speed. This is illustrated in FIGS. 18A-B, which show multiple laser beams used sequentially to form multiple laser focus spots in the IOL. In the case of FIG. 18A, the incident laser beams are all parallel to the optical axis. Due to the focusing power of the IOL, the beams are bent by the IOL toward the optical axis, and as a result, the multiple laser beams will fall on a smaller retinal area than had the beams remained parallel to the optical axis after the IOL. In the case of FIG. 18B, the laser beams are incident on the IOL in directions non-parallel to the optical axis (they travel away from the optical axis); after these laser beams are bent toward the optical axis by the focusing power of the IOL, they become more parallel to the optical axis than in the case of FIG. 18A and consequently fall on a retinal area that is larger than in the case of FIG. 18A. Larger retinal spot sizes allow higher laser average power and with that faster processing speed. The desired amount of pre-compensation may be determined by numerical simulation.

The heat induced refractive index change in IOL materials may be positive or negative, depending on the laser energy and other parameters, and may change with time after laser irradiation. After a certain time, such as one day, the change of refractive index will stabilize. Different IOL materials also respond differently to the laser treatment. For example, the final index change is mostly positive for the SENSAR® IOL material, but may be negative for some other IOL materials, such as for example, acrylic IOL materials having a higher water content. The amount of induced refractive index change may be measured for each IOL material, for example, using a phase shifting interferometer.

Figure 19:
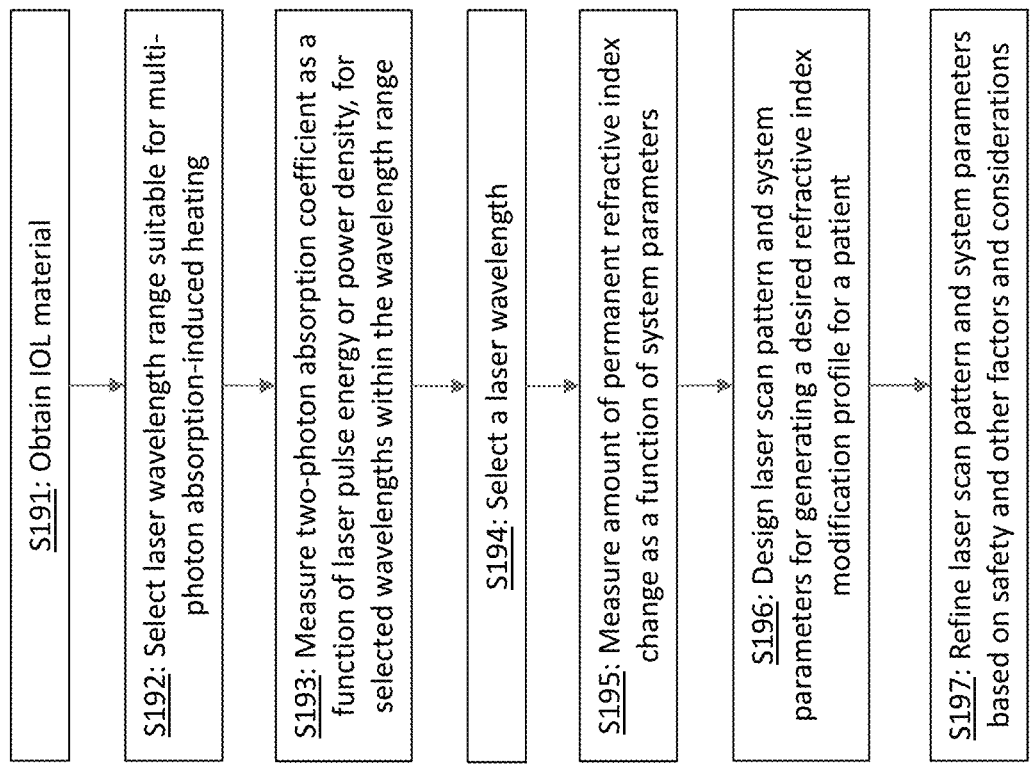
FIG. 19 is a flow chart illustrating a refractive index modification method according to an embodiment of the present invention.

In practice, for a given IOL material, the amount of induced refractive index change, as a function of laser energy and other parameters such as NA, laser pulse duration, laser repetition rate and pattern (such as spot spacing and timing, due to thermal lensing), laser wavelength, etc., is empirically determined. Based on such data, the laser parameters and scan pattern can be designed to achieve a given target result of desired refractive index modification of the IOL. More specifically, as shown in FIG. 19, for a given IOL material (step S191), its linear absorption coefficient is examined to preliminarily select a laser wavelength range that may potentially be suitable for multi-photon induced heating (step S192). The sensitivity of the eye for different wavelength ranges is taken into consideration in this step. For example, FIG. 11, described earlier, illustrates how the suitable wavelength range is preliminarily selected for the SENSAR® IOL material. Then, the two-photon absorption coefficient of the material as a function of laser pulse energy (or average power density) is measured for selected wavelengths within the preliminarily selected wavelength range (step S193). This may be done, for example, by measuring the light transmission rate through the sample as a function of pulse energy or power and then fitting the curves to obtain the threshold and coefficient parameters. An example of this step for the SENSAR® IOL material is described earlier with reference to FIGS. 12 and 13A-13B. Based on such data, a laser wavelength may be selected to perform refractive index modification for this material (step S194). Then, the amount of permanent refractive index change of the material as a function of various system parameters is measured (step S195). For example, a phase shifting interferometer may be used for such measurement, as described earlier with reference to FIG. 18 as well as FIGS. 6A-9C. With the above data, a laser scan pattern and other laser system parameters can be designed to produce a desired refractive index modification profile (step S196). The system parameters may include, for example, laser pulse energy, pulse duration, pulse repetition rate, focus spot size, numerical aperture, etc. The scan pattern parameters may include, for example, geometric shape formed by the laser irradiation spots, spot spacing, etc. In this step, the selection of the various parameters may take into consideration of exposure safety limits for the eye. In addition, the designed laser scan pattern and system parameters may be refined based on other factors and considerations (step S197), such as the self-limiting effect of multi-photon absorption on the absorption depth described earlier with reference to FIGS. 14A-14D and FIG. 15, the self-limiting effect caused by thermal lensing described earlier with reference to FIG. 16, consideration of thermal load distribution described earlier with reference to FIGS. 17A-17B, etc. The refinement may be achieved based on numerical simulations of the various effects discussed above.

Figure 20:
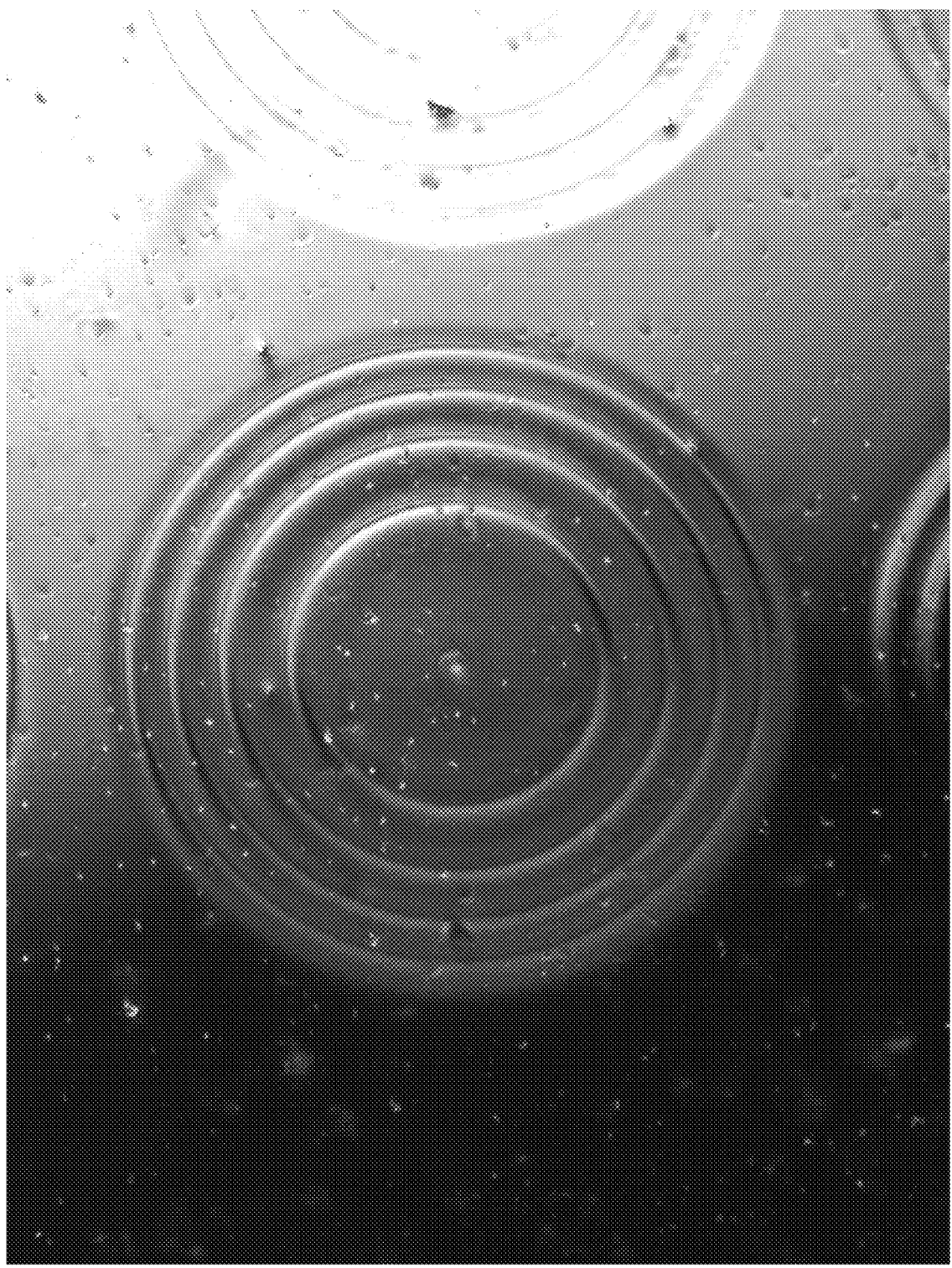
FIG. 20 illustrates an exemplary index Fresnel lens formed in an IOL material by refractive index modification according to an embodiment of the present invention.
Figure 21:
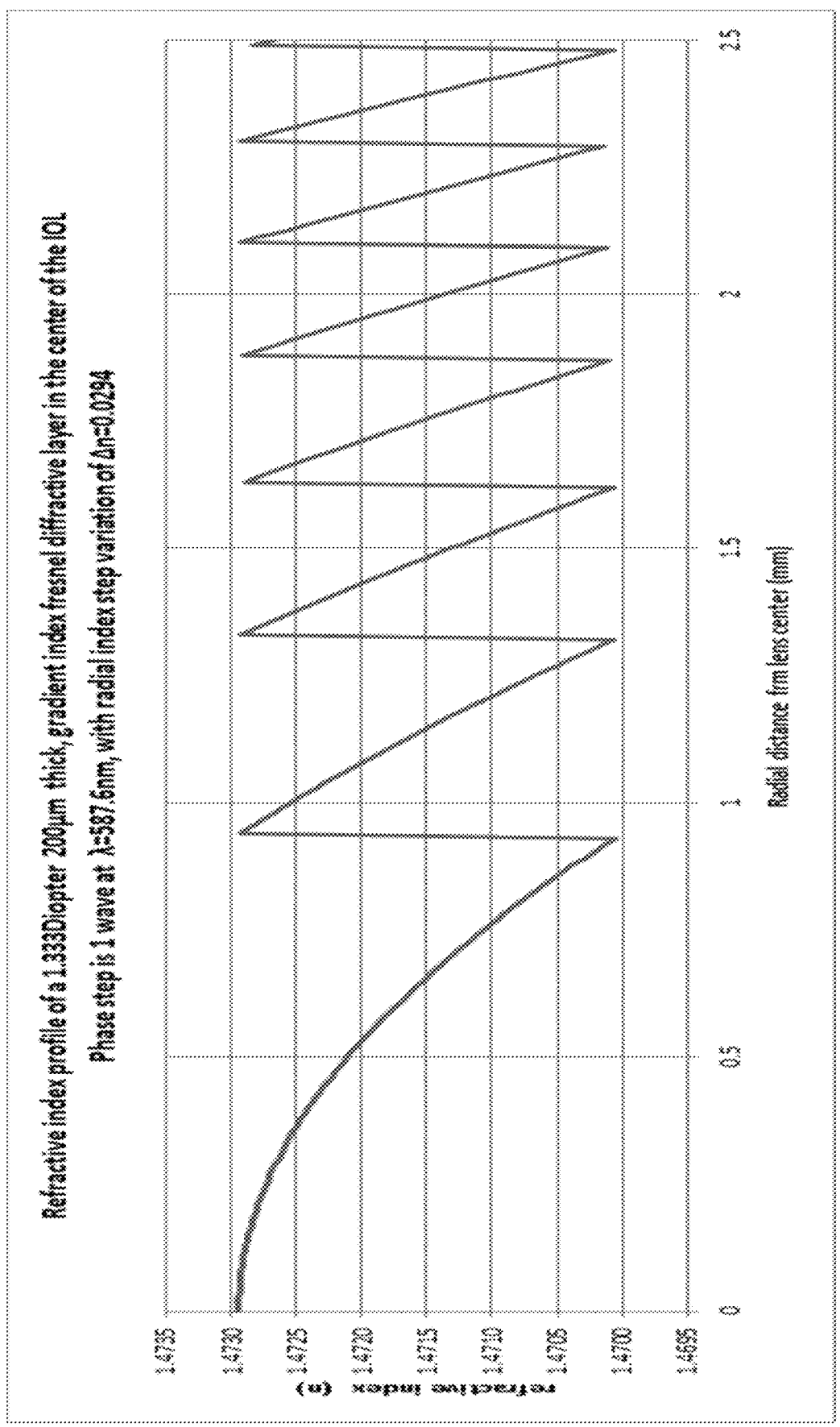
FIG. 21 shows an example of a Fresnel refractive index profile along a radial direction according to an embodiment of the present invention.

In an alternative embodiment, by scanning the pulsed laser beam in the IOL in concentric patterns, concentric rings of refractive index variation may be generated, forming a Fresnel lens. Such a lens may provide high optical power changes (it adds an optical power to the optical power of the IOL), as high as multiple diopters. In one example, a Fresnel lens formed this way (see FIG. 20) has 6 D absolute power as measured by phase shifting interferometry as well as wavefront measurements. FIG. 21 shows an example of a Fresnel refractive index profile along a radial direction from the lens center. To be a Fresnel lens, the phase step, i.e. the size of the jumps between zones in the index profile, should be an integer number of waves. In this particular example, the IOL is made of SENSAR® IOL material, and has an edge thickness of 400 µm and a center thickness of 722 µm. A layer of the SENSAR® IOL material 200 µm thick is modified by the laser with a variable index in a number of annular zones (7 in this case) centered on the optical axis of the IOL. Each zone has a 1 wave difference in phase from the inner to the outer edge of the zone, and a 1 wave step transitioning to the next zone. For example, a 7-zone gradient index, Fresnel diffractive lens with a diameter of about 5 mm, has an optical power of 1.333 Diopters. The radial profile in phase has 7 zones of 1 wave steps, requiring the gradient refractive index profile shown in the figure within the 200 µm layer. The example shows a parabolic index profile with one wave stepping.

As discussed above, the change in refractive index of the IOL in response to laser treatment depends on a multitude of factors, and at the same time, the laser treatment is limited by various eye safety concerns. Therefore, suitable laser system parameters for a refractive index modification procedure may vary greatly. In some embodiments, for the SENSAR® IOL material, the various laser system parameters fall within the following preferred ranges. Laser wavelength: 650 to 800 nm, more preferably, 680 to 720 nm; laser pulse energy: 10 nJ to 10 uJ, more preferably, 100 nJ to 2 uJ; laser pulse duration: 10 fs to 10 ps, more preferably, 100 to 600 fs; laser pulse repetition rate: 10 to 1000 kHz, more preferably, about 300 kHz; laser focus spot size: 5 to 25 um, more preferably, 7 to 12 um; numerical aperture (NA) of the incident beam: 0.01 to 0.15, more preferably, 0.03 to 0.12; number of repeats (successive laser pulses irradiated at the same position): 1 to 14. For the laser scan pattern, the spot spacing in the transverse direction will typically change with focus spot size and repetition rate; the spot spacing should be sufficiently small to create substantially uniform index change zone throughout. For a beam with a Gaussian profile, the spot spacing is preferably smaller than the beam spot size. The spot spacing may be different in different scan directions of the scan pattern. In the depth direction, the spot separation is 1 to 100 um, and more preferably, 3 to 10 um.

In one particular example that used a circular scan pattern, the spot spacing was 2.5 um in the angular direction and 4 um in the radial direction (i.e. between adjacent circles of the scan pattern), and the beam had a super-Gaussian profile with an 8 um diameter. In this example, the pulse energy was 0.9 uJ, a total of 10.8 J of energy was deposited in a 20 mm$^2$ area, and the treatment time 0.1 W power was 108 seconds. The phase change generated by one layer of modification was about 0.06λ, and about 1.2λ for 20 layers.

In summary, the use of multi-photon absorption allows for the use of high absorption of the IOL material in the UV/blue spectral and in the far red spectral range, where the photopic sensitivity of the eye is relatively low. The use of laser wavelengths outside the spectral sensitivity of the human eye allows treatment of patients without the significant visual effects during patient exposure and good patient compliance during the laser treatment. Due to the short pulse duration needed to get a two photon absorption, effective heating shorter than the thermal relaxation time is enabled. Additionally, due to the non-linear absorption of two or more photons, the exposure in the laser focal volume is self-limiting as the laser light upfront of the laser focus will start to be absorbed as soon as the threshold of multiphoton absorption is reached. Further, the effect of thermal lensing, i.e. the defocusing of subsequent neighboring laser spots in the scan pattern due to thermal lensing caused by the previous laser pulses, may be avoided by placing subsequent laser pulse spots outside of the thermal impact zone of the previous pulses; the thermal lensing effect may also be taken advantage of to defocus the laser spots which allows for higher pulse energy to be used. Also, the overall thermal management of the induced thermal load within the IOL and surrounding tissue becomes and important practical consideration, as overloading the IOL and surrounding tissue with heat should be avoided to avoid thermal damage.

The refractive index modification methods described above may also be used for customization of IOLs during production, or in-office modification after production but before implantation into patients' eyes. In such applications, the wavelength restrictions and the eye safety considerations are eliminated because no patient's sys is present, and higher laser power may be used to increase the processing speed. In an in-office modification process, the target refractive index modification is customized for the intended patient, and the laser scan patterns is designed to achieve such a target modification.

Figure 22:
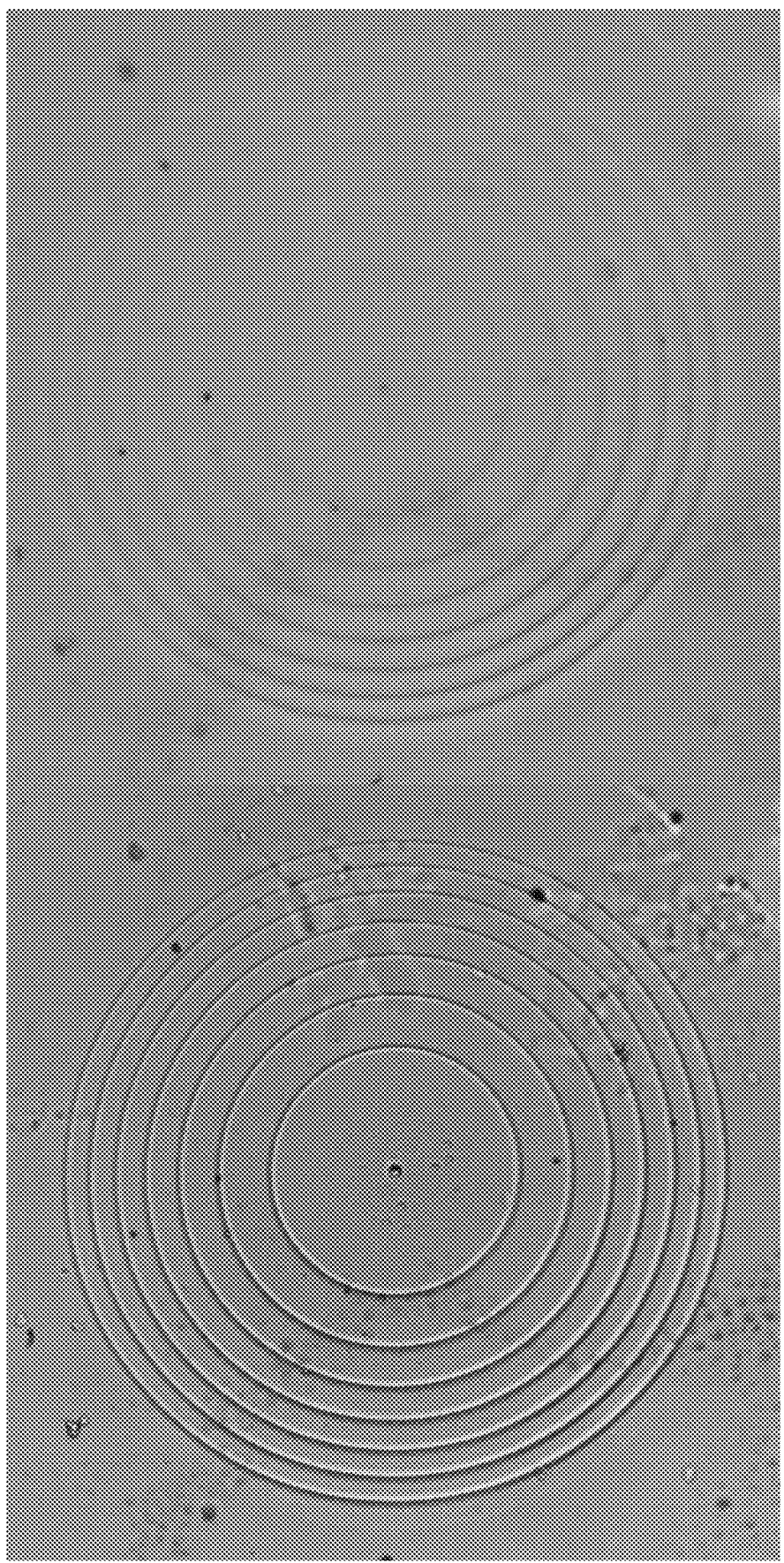
FIGS. 22A and 22B show an example of a Fresnel lens formed in a contact lens according to an embodiment of the present invention.

In addition to IOLs, the refractive index modification methods described above may also be used to modify the refractive properties of contact lenses. FIGS. 22A (phase contrast) and 22B (bright field) shows a Fresnel lens pattern written in a contact lens, in this example, an Etafilcon A contact lens with 58% water, 1 day Acuvue Moist, with 50-125 nJ pulse energy and 12 pattern repeats. This method can be used to customize contact lenses.

In various embodiments described above, the methods for modifying refractive index of the IOL material may be carried out by the laser system describe earlier which includes the control electronics 210. The control electronics 210 may include a computer, microcontroller, etc., and associated memory devices that store computer readable program code. The computer or microcontroller executes the computer readable program code to control the laser light source 200 and other components of the laser system 200 to execute the above described methods.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

The invention claimed is:

1. A method of altering a refractive property of an implantable intraocular lens having an optic body including an optical zone and a peripheral zone surrounding the optical zone, comprising:
   generating a pulsed laser beam using a pulsed laser source and a light delivery optical system, the pulsed laser beam including a plurality of laser pulses; and
   irradiating the optical zone of the intraocular lens with the light beam by delivering focus spots of the laser pulses within the optical zone,
   wherein the laser pulses includes a first plurality of laser pulses each having a first pulse energy configured to modify a refractive index of the optical zone, and a second plurality of laser pulses each having a second pulse energy which is $1/100$ to $1/10$ of the first pulse energy, wherein the first plurality of laser pulses are delivered to the optical zone according to a scan pattern, and each of the second laser pulses is delivered to the optical zone at a location related to a corresponding one of the plurality of first laser pulses and precedes the corresponding first laser pulse by a predetermined time interval, whereby each second laser pulse heats the optical zone to form a transient thermal lens that defocuses the corresponding first laser pulse;
   wherein the optical zone comprises a material configured to change its refractive index upon irradiation by the first plurality of laser pulses, thereby altering a refractive property of the intraocular lens.

2. The method of claim 1, wherein the optical zone comprises a crosslinked acrylic material, and wherein irradiation with the light beam produces a predetermined change in the refractive index of the crosslinked acrylic polymer.

3. The method of claim 2, wherein the change in refractive index relative to the pre-irradiation refractive index at a location within the crosslinked acrylic polymer is linearly related with a total energy of the irradiation with the light source within a defined total energy range.

4. The method of claim 1, further comprising:
   before the irradiating step, implanting the intraocular lens in a patient's eye, wherein the irradiating step is performed while the intraocular lens is in the patient's eye.

5. The method of claim 1, wherein the irradiating step is performed while the intraocular lens is outside of any patient's eye.

6. The method of claim 1, wherein the predetermined time interval is 100 ps to 100 ns.

* * * * *